US008236309B2

(12) United States Patent
Bigler et al.

(10) Patent No.: US 8,236,309 B2
(45) Date of Patent: Aug. 7, 2012

(54) USE OF BISPECIFIC ANTIBODIES TO REGULATE IMMUNE RESPONSES

(75) Inventors: Michael Eric Bigler, Redwood City, CA (US); Holly Marie Cherwinski, Boulder Creek, CA (US); Joseph H. Phillips, Palo Alto, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/787,044

(22) Filed: May 25, 2010

(65) Prior Publication Data
US 2010/0330034 A1    Dec. 30, 2010

Related U.S. Application Data

(63) Continuation of application No. 10/270,084, filed on Oct. 11, 2002, now abandoned.

(60) Provisional application No. 60/329,182, filed on Oct. 12, 2001.

(51) Int. Cl.
*A61K 39/395*    (2006.01)

(52) U.S. Cl. .................................... 424/136.1

(58) Field of Classification Search .......... None
See application file for complete search history.

(56) References Cited

U.S. PATENT DOCUMENTS

| | | | |
|---|---|---|---|
| 4,946,778 A | 8/1990 | Ladner et al. | |
| 6,197,298 B1 | 3/2001 | Chang | |
| 6,338,851 B1 | 1/2002 | Gorczynski | |
| 6,476,195 B1 | 11/2002 | Komatsoulis et al. | |
| 6,652,858 B2 | 11/2003 | Gorczynski et al. | |
| 6,749,854 B2 | 6/2004 | Gorczynski et al. | |
| 6,955,811 B2 | 10/2005 | Gorczynski et al. | |
| 6,984,625 B2 | 1/2006 | Gorczynski | |
| 7,118,743 B2 | 10/2006 | Thomas et al. | |
| 7,186,818 B2 | 3/2007 | Van Der Vuurst De Vries et al. | |
| 7,205,386 B2 | 4/2007 | Gorczynski | |
| 7,223,729 B2 | 5/2007 | Gorczynski | |
| 7,368,535 B2 | 5/2008 | Gorczynski et al. | |
| 2002/0192215 A1 | 12/2002 | Hoek et al. | |
| 2003/0077282 A1 | 4/2003 | Bigler et al. | |
| 2003/0223991 A1 | 12/2003 | Cherwinski et al. | |
| 2004/0126777 A1 | 7/2004 | Bhatt et al. | |
| 2004/0198661 A1 | 10/2004 | Bowdish et al. | |
| 2004/0213783 A1 | 10/2004 | Liversidge et al. | |
| 2005/0074452 A1 | 4/2005 | Bowdish et al. | |
| 2005/0169870 A1 | 8/2005 | Truitt et al. | |
| 2005/0287603 A1 | 12/2005 | Gorczynski | |
| 2006/0084121 A1 | 4/2006 | Barclay et al. | |
| 2006/0240010 A1 | 10/2006 | Cherwinski et al. | |
| 2007/0244052 A1 | 10/2007 | Zhang et al. | |

FOREIGN PATENT DOCUMENTS

| | | |
|---|---|---|
| EP | 0255249 | 2/1988 |
| EP | 0339379 | 10/1989 |
| WO | WO98/29543 | 7/1998 |
| WO | WO99/42077 | 8/1999 |
| WO | WO00/06698 | 2/2000 |
| WO | WO00/29431 | 5/2000 |
| WO | WO00/61171 | 10/2000 |
| WO | WO00/70045 | 11/2000 |
| WO | WO01/36463 | 5/2001 |
| WO | WO02/088164 | 11/2002 |
| WO | WO03/077947 | 1/2003 |
| WO | WO03/064662 A1 | 8/2003 |
| WO | WO2004/060295 | 7/2004 |
| WO | WO2005/074985 | 8/2005 |

OTHER PUBLICATIONS

Akbari, et al, "Pulmonary Dendritic Cells Producing IL-10 Mediate Tolerance Induced by Respiratory Exposure to Antigen", Nat. Immunol., vol. 2, pp. 725-731 (2001).
Alonso et al, Stem Cell of the Skin Epithelium, Proc. Natl. Acad. Sci. USA, vol. 100, pp. 11830-11835 (2003).
Amato et al, Cicatrical Alopecia; a Dermatopathologic and Immunopathologic Study of 33 Patients (Pseudopelade of Brocq is Not a Specific Clinico-Pathologic Entity, Int. J. Dermatol, vol. 41, pp. 8-15 (2002).
Arm et al, "Molecular Identification of a Novel Family of Human Ig Superfamily Members That Possess Immunoreceptor Tyrosine-Based Inhibition Motifs and Homology to the Mouse gp49B1 Inhibitory Receptor", J. Immunol., vol. 159, pp. 2342-2349 (1997).
Askenase et al, "Defective Elicitation of Delayed-Type Hypersensitivity in W/W and SI/SI Mast Cell-Deficient Mice", The Journal of Immunology, vol. 131, No. 6, pp. 2687-2694 (1983).
Avichezer et al, "Identification of a New Epitope of Human IRBP that Induces Autoimmune Uveoretinitis in Mice of the H-$2^b$ Haplotype", Invest. Ophthalmol. Vis. Sci., vol. 41, pp. 127-131 (2000).
Azzam et al, "Fine Tuning of TCR Signaling by CD5" J. Immunol., vol. 166, pp. 5464-5472 (2001).
Azzoni et al, "Differential Transcriptional Regulation of CD161 and a Novel Gene, 197/15a, by IL-2, IL-15, and IL-12 in NK and T Cells", J. Immunol., vol. 161, pp. 3493-3500 (1998).
Bai et al, "Nasal Tolerance Induction as a Potential Means of Immunotherapy for Autoimmune Diseases: Implications for Clinical Medicine", Clinical and Experimental Allergy, vol. 30, pp. 1688-1696 (2000).
Bakker et al, "Myeloid DAP-12-associating Lectin (MDL)-1 is a Cell Surface Receptor Involved in the Activation of Myeloid Cells", Proc. Natl. Acad. Sci. USA, vol. 96, No. 17, pp. 9792-9796 (1999).
Barclay et al, "Purification and Chemical Characterisation of Membrane Glycoprotiens from Rat Thymocytes and Brain, Recognised by Monoclonal Antibody MRC OX2", Eur. J. Biochem., vol. 129, pp. 447-458 (1982).
Barclay, et al, "CD200 and Membrane Protein Interactions in the Control of Myeloid Cells", Trends Immunol, vol. 23, No. 6, pp. 285-290 (2002).
Bazan et al, "A Newly Defined Interleukin-1?", Nature, vol. 379, pp. 591 (1996).

(Continued)

*Primary Examiner* — Ilia Ouspenski

(57) ABSTRACT

The invention relates generally to the field of immunology, in particular, to bispecific antibodies. Methods for designing a bispecific antibody for use in treating diseases relating to the immune system are disclosed. Specific examples relate to bispecific antibodies which recognize an activating receptor and an inhibiting receptor.

9 Claims, No Drawings

OTHER PUBLICATIONS

Bergfeld, et al, "Alopecia: Histologic Changes", Dermatol., vol. 4, pp. 301-320 (1969).
Billingham, "Transplantation Immunity Evoked by Skin Homografts and Expressed Intact Skin", Adv. Biol. Skin, vol. 11, pp. 183-196 (1971).
Billingham et al, "A Biologists Reflections on Dermatology", J. Invest. Dermatol., vol. 57, No. 4, pp. 227-240 (1971).
Birch et al, Female Pattern Hair Loss, Clin. Exp. Dermatol., vol. 27, pp. 383-388 (2002).
Black, Judith, "The Role of Mast Cells in the Pathophysiology of Asthma", New England Journal of Medicine, vol. 346, No. 22, pp. 1742-1743 (2002).
Blaser et al, "Cutting Edge: Virus-Activated CD8 T Cells and Lymphokine-Activated NK Cells Express the Mast Cell Function-Associated Antigen, An Inhibitory C-Type Lectin", J. Immunol., vol. 161, pp. 6451-6454 (1998).
Blazer et al. J. Immunol. 1996; 157:3250-3259.
Blery, Mathieu, et al., J. Biol. Chem., 272(14):8989-8996, Apr. 4, 1997. "Reconstituted killer cell inhibitory for major histocompatibility complex class I molecules control mast cell activation induced via immunoreceptor tyrosine-based activation motifs".
Bodemer et al, "Role of Cytotoxic T Cells in chronic Alopecia AreataJ", J. Invest. Dermatol., vol. 114, pp. 112-116 (2000).
Borges et al, "A Family o f Human Lymphoid and Myeloid Ig-Like Receptors, Some of Which Bind to MHC Class I Molecules", J. Immunol., vol. 159, pp. 5192-5196 (1997).
Bork, "Powers and Pitfalls in Sequence Analysis: the 70% Hurdle", Genome Research, vol. 10, pp. 348-400 (2000).
Borriello et al, "MRC OX-2 Defines a Novel T Cell Costimulatory Pathway", J. Immunol., vol. 158, pp. 4548-4554 (1997).
Borriello et al, "Characterization and Localization of Mox2, the Gene Encoding the Murine Homolog of the Rat MRC OX-2 Membrane Glycoprotein", Mamm. Genome, vol. 9, pp. 114-118 (1998).
Botchikarev et al, "Developmentally Regulated Expression of α-MSH and MC-1 Receptor in C57BL/6 Mouse Skin Suggests Functions Beyond Pigmentation", Ann. N.Y. Acad. Sci., vol. 885, pp. 433-439 (1999).
Braun, et al, "Manipulation of Stem Cell Proliferation and Lineage Commitment: Visualization of Label-Retaining Cells in Wholemounts of Mouse Epidermis," Development, vol. 130, pp. 5241-5255 (2003).
Brennan et al, "Preparation of Bispecific Antibodies by Chemical Recombination of Monoclonal Immunoglobulin G1 Fragments", Science, vol. 229, pp. 81-83 (1985).
Brenner, "Errors in genome Annotation", TIG, vol. 15, pp. 132-133 (1999).
Broderick, et al, "Constitutive Retinal CD200 Expression Regulates Resident Microglia and Activation State of Inflammatory Cells during Experimental Autoimmune Uveoretinitis", Am. J. Pathol., vol. 161, pp. 1669-1677 (2002).
Broun et al, "Catalytic Plasticity of Fatty Acid Modification Enzymes Underlying Chemical Diversity of Plant Lipids", Science, vol. 282, pp. 1315-1317 (1998).
Bruhns et al, "Differential Roles of N- and C-Terminal Immunoreceptor Tyrosine-Based Inhibition Motifs during Inhibition of Cell Activation by Killer Cell Inhibitory Receptors", Journal of Immunology, vol. 162, pp. 3168-3175 (1999).
Bruhns et al, Molecular Basis of the Recruitment of the SH2 Domain-Containing Inositor 5-Phosphatases SHIP1 and SHIP2 by FeγRIIBJ. Biol. Chem., vol. 275, pp. 37357-37364 (2000).
Burkhart et al, "Peptide-Induced T Cell Regulation of Experimental Autoimmune Encephalomyelitis: A Role for IL-10", Int. Immunol., vol. 11, No. 10, pp. 1625-1634 (1999).
Byrne et al, "Programming Gene Expression in Developing Epidermis", Development, vol. 120, pp. 2369-2383 (1994).
Busse et al, "Asthma", The New England Journal of Medicine, vol. 344, No. 5, pp. 350-362 (2001).
Cambier, "Inhibitory Receptors Abound?", Proceedings of the National Academy of Sciences of the United States of America, vol. 94, No. 12, pp. 5993-5995 (1997).
Campbell et al, "DAP12 a Key Accessory Protein for Relayhing Signals by Natural Killer Cell Receptors", Int. J. Biochem. Cell Biol., vol. 31, No. 6, pp. 631-636 (1999).
Cant et al, "Signal Regulation by Family Conspiracy", Cell Mol. Life Sci., vol. 58, pp. 117-124 (2001).
Carter, Paul, J. Immunol Methods, 248(1-2):7-15, Feb. 1, 2001. "Bispecific human IgG by design".
Chaiken etal, "Identifying Structure-Function Relationships in Four-Helix bundle Cytokines: Towards de novo Mimetics Design", Trends Biotechnol., vol. 14, No. 10, pp. 369-375 (1996).
Chen et al, "Cloning and Characterization of the Murine Homologue of the Rat/Human MRC OX-2 Gene", Biochim. Biophys. Acta, vol. 1362, pp. 6-10 (1997).
Cherwinski et al, "The CD200 Receptor is a Novel and Potent Regulator of Murine and Human Mast cell Function", Journal of Immunology, vol. 174, pp. 1348-1356 (2005).
Chieregato et al, "Lichen Planopilaris: Report of 30 Cases and Review of the Literature", Int. J. Dermatol., vol. 42, pp. 342-345 (2003).
Christoph et al, "The Human Hair Follicle Immune System: Cellular Composition and Immune Privilege", Br. J. Dermatol., vol. 142, pp. 862-873 (2000).
Claesson et al, "The Influence of the Hair Follicle Phase on the Survival Time of Skin Allografts in the Mouse", Transplantation, vol. 10, pp. 349-351 (1970).
Coggeshall, "Inhibitory Signaling by B Cell FcγRllb" Curr. Opinion Immunol., vol. 10, pp. 306-312 (1998).
Davidson et al, "Autoimmune Diseases", New Engl. J. Med., vol. 345, pp. 340-350 (2001).
Di Cristofano, et al, "Molecular Cloning and Characterization of $p56^{dok-2}$ Defines a New Family of RasGAP-Binding Proteins", J. Biol. Chem., vol. 273, No. 9, pp. 4827-4830 (1998).
Dick et al, "Nasal Administration of Retinal Antigens Suppresses the Inflammatory Response in Experimental Allergic Uveoretinitis", British Journal of Ophthalmology, vol. 77, pp. 171-175 (1993).
Dick et al, "Immunomodulation of Experimental Autoimmune Uveoretinitis: A Model of Tolerance Induction with Retinal Antigens", Eye, vol. 8, Pt. 1, pp. 52-59 (1994).
Dick et al, "Intranasal Administration of Retinal Antigens Suppresses Retinal Antigen-Induced Experimental Autoimmune Uveorentinitis", Immunology, vol. 82, pp. 625-631 (1994).
Dick et al, "Inhibition of Tumor Necrosis Factor Activity Minimizes Target Organ Damage in Experimental Autoimmune Uveoretinitis Despite Quantitatively Normal Activated T Cell Traffic to the Retina", Eur. J. Immonol., vol. 26, pp. 1018-1025 (1996).
Dick et al, "Immune Regulation of Uveoretinal Inflammation", Dev. Ophthalmol., vol. 30, pp. 187-202 (1999).
Dick et al, "Immune Mechanisms of Uveitis: Insights Into Disease Pathogenesis and Treatment", Int. Ophthalmol. Clin., vol. 40, No. 2, pp. 1-18 (2000).
Dick, et al, "Single Dose Intranasal Administration of Retinal Autoantigen Generates a Rapid Accumulation and Cell Activation in Draining Lymph Node and Spleen: Implications for Tolerance Therapy", Br. J. Ophthalmol., vol. 85, pp. 1001-1006 (2001).
Dick, et al, "Control of Myeloid Activity During Retinal Inflammation", J. Leukoc. Biol., vol. 74, No. 2, pp. 161-166 (2003).
Dietrich et al, "Cutting Edge: Signal-Regulatory Protein β1 Is a DAP12-Associated Activating Receptor Expressed in Myeloid Cells", J. Immunol., vol. 164, pp. 9-12 (2000).
Dick et al, "Distribution of IX2 Antigen and OX2 Receptor within Retina", Investigative Ophthalmology & visual Science, vol. 42, No. 1, pp. 170-176 (2001).
Donnadieu et al, "Reconstitution of CD3ζ Coupling to Calcium Mobilization via Genetic Complementation", Proc. Natl. Acad. Sci., vol. 269, pp. 32828-32834 (1994).
Eichmuller et al, "Clusters of Perifollicular Macrophages in Normal Murine Skin: Physiological Degeneration of Selected Hair Follicles by Programmed Organ Deletion", J. Histochem. Cytochem., vol. 46, pp. 361-370 (1998).
El Darouti et al, "Eosinophils in Fibrous Tracts and Near Hair Bulbs: A Helpful Diagnostic Feature of Alopecia Areata", J. Am. Acad. Dermatol., vol. 42, pp. 305-306 (2000).

Elston et al, "Eosinophils in Fibrous Tracts and Near Hair Bulbs: A Helpful Diagnostic Feature of Alopecia Areata", J. Am. Acad. Dermatol., vol. 37, pp. 101-106 (1997).

Erwig et al, "Initial Cytokine Exposure Determines Function of Macrophages and Renders Them Unresponsive to Other Cytokines", J. Immunol., vol. 161, pp. 1983-1988 (1998).

Fournier et al, "FDF03, a Novel Inhibitory Receptor of the Immunoglobulin Superfamily, Is Expressed by Human Dendritic and myeloid Cells", J. Immunol., vol. 165, pp. 1197-1209 (2000).

Forrester et al, "Marrow-Derived Activated Macrophages are Required During the Effector Phase of Experimental Autoimmune Uveoretinitis in Rats", Curr. Eye Res., vol. 17, pp. 426-437 (1998).

Foster-Cuevas et al, "Human Herpesvirus 8 K14 Protein Mimics CD200 in Down-Regulating Macrophage Activation Through CD200 Receptor", Journal of Virology, vol. 78, No. 14, pp. 7667-7676 (2004).

Gérard, et al, "Functional Interaction of RasGAP-Binding Proteins Dok-1 and Dok-2 with the Tec Protein Tyrosine Kinase", Oncogene, vol. 23, No. 8, pp. 1594-1598 (2004).

Gilhar et al, "Autoimmune Hair Loss (Alopecia Areata) Transferred by Tlymphocytes to Human Scalp Explants on SCID Mice", J. Clin. Invest., vol. 101, pp. 62-67 (1998).

Goerdt et al, "Other Functions, Other Genes: Alternative Activation of Antigen-Presenting Cells", Immunity, vol. 10, pp. 137-142 (1999).

Gergely, Janos, et al., Immunology Lett., 68(1):3-15, May 3, 1999. "Immunoreceptor tyrosine-based inhibition motif-bearing receptors regulate the immunoreceptor tyrosine-based activation motif-induced activation of immune comptent cells."

Gorczynski et al, "Increased Expression of the Novel Molecule OX-2 is involved in Prolongation of Murine Renal Allograft Survival", Transplantation, vol. 65, No. 8, pp. 1106-1114 (1998).

Gorczynski et al, "An Immunoadhesin Incorporating the Molecule OX-2 is a Potent Immunosuppressant that Prolongs Allo- and Xenograft Survival", The Journal of Immunology, vol. 163, pp. 1654-1660 (1999).

Gorczynski et al, "Receptor Engagement of Cells Expressing a Ligand for the Tolerance-Inducing Molecule OX2 Induces an Immunoregulatory Population That Inhibits Alloreactivity In Vitro and In Vivo", The Journal of Immunology, vol. 165, pp. 4854-4860 (2000).

Gorczynski et al, "Evidence for Persistent Expression of OX2 as a Necessary Component of Prolonged Renal Allograft Survival Following Portal Vein Immunization", vol. 97, No. 1, pp. 69-78 (2000).

Gorczynski et al, "Synergy in Induction of Increased Renal Allograft Survival After Portal Vein Infusion of Dendritic Cells Transduced to Express TGFB and IL-10, Along with Administration of CHO Cells Expressing the Regulatory Molecule OX-2", Clinical Immunology, vol. 95, No. 3, pp. 182-189 (2000).

Gorczynski, Transplant Tolerance Modifying Antibody to CD200 Receptor, But Not CD200, Alters Cytokine Production Profile from Stimulated Macrophages:, Eur. J. Immunology, vol. 31, pp. 2331-2337 (2001).

Gorczynski, Evidence for an Immunoregulatory Role of OX2 with its Counter Ligand (OX2L) in the Regulation of Transplant Rejection, Fetal Loss, Autoimmunity and Tumor Growth:, Archivum Immunologiae et Therapiae Experimentalis, vol. 49, pp. 303-309 (2001).

Gorczynski et al, "Evidence of a Role for CD200 in Regulation of Immune Rejection of Leukaemic Tumor Cells in C57BL/6 Mice", Clin. Exp. Immunology, vol. 126, pp. 220-229 (2001).

Gorczynski et al, "CD200 Immunoadhesin Suppresses Collagen-Induced Arthritis in Mice", Clinical Immunology, vol. 101, No. 3, pp. 328-334 (2001).

Gorczynski et al, "A CD200FC Immunoadhesin Prolongs Rat Islet Xenograft Survival in Mice", Transplantation, vol. 73, No. 12, pp. 1948-1953 (2002).

Gorczynski, "Anti-CD200R Ameliorates Collagen-Induced Arthritis in Mice", Clin. Immunol., vol. 104, No. 3, pp. 256-264 (2002).

Gosselin et al, "Induction of DAP12 Phosphorylation, Calcium Mobilization, and Cytokine Secretion by Ly49H", J. Leukoc. Biol., vol. 66, No. 1, pp. 165-171 (1999).

Greenwald et al, "Negative Co-Receptors on Lymphocytes", Curr. Opin. Immunol., vol. 14, pp. 391-396 (2002).

Guthmann et al, "A Secretion Inhibitory Signal transduction Molecule on Mast Cells is Another C-Type Lectin", Proc. Natl. Acad. Sci., vol. 92, pp. 9397-9401 (1995).

Harrist et al, "Distribution of Major Histocompatibility Antigens in Normal Skin", Br. J. Dermatol., vol. 109, pp. 623-633 (1983).

Heath et al, "The Human A33 Antigen is a Transmembrane Glycoprotein and a Novel Member of the Immunoglobulin Superfamily", Proc. Natl. Acad. Sci. USA, vol. 94, No. 2, pp. 469-474 (1997).

Herz et al, "Molecular Approaches to Receptors as Targets for Drug Discovery", J. Recept Signal Transduct Res., vol. 17, No. 5, pp. 671-776 (1997).

Hoek, Robert M., et al., Science., 290(5497):1768-1771, Dec. 1, 2000. "Down-regulation of the macrophage lineage through interaction with OX2 (CD200)".

Hoey et al, "Nitric Oxide Accelerates the Onset and Increases the Severity of Experimental Autoimmune Uveoretinitis Through and IFN-γ-Dependent Mechanism", J. Immunol., vol. 159, pp. 5132-5142 (1997).

Hoffman et al, "Cytokine mRNA Levels in Alopecia Areata Before and After Treatment With the Contact Allergen Diphenylcyclopropenone", J. Invest. Dermatol., vol. 103, pp. 530-533 (1994).

Hoffman, "The Potential Role of Cytokines and T Cells in Alopecia Areata", J. Investig. Dermatol. Symp. Proc., vol. 4, pp. 235-238 (1999).

Hoffman et al, "Male Androgenetic Alopecia", Clin. Exp. Dermatol., col. 27, pp. 373-382 (2002).

Holliger, Philipp, et al., Cancer Immunol. Immunother., 45(3-4):128-30, Nov.-Dec. 1997. "Diabodies: small bispecific antibody fragments."

Hudson, Peter J., et al., J. Immunol. Methods, 231(1-2):177-189, Dec. 10, 1999. "High avidity scFv multimers; diabodies and triabodies."

Idusogie et al, "Mapping of the C1q Binding Site on Rituxan, a Chimeric Acntibody with a Huma IgG1 Fc", J. Immunol., vol. 164, pp. 4178-4184 (2000).

Ihle et al, "Jaks and Stats in Cytokine Signaling", Stem Cells, vol. 15, Supp. 1, pp. 105-111 (1997).

International Search Report issued in corresponding PCT/US02/32711 (Aug. 12, 2003).

Janes et al, "Epidermal Stem Cells", J. Pathol., vol. 197, pp. 479-491 (2002).

Jiang et al, "Macrophages and Dendritic Cells in IRBP-Induced Experimental Autoimmune Uveoretnitis in BI0RIII Mice", Invest. Ophthalmol., Vis. Sci., vol. 40, pp. 3177-3185 (1999).

Jiang et al, "Total Dose and Frequency of Administration Critically Affect Success of Nasal Mucosal Tolerance Induction", Br. J. Ophthalmol., vol. 85, pp. 739-744 (2001).

Kalesnikoff et al, "Monomeric IgE Stimulates Signaling Pathways in Mast Cells that Lead to Cytokine Production and Cell Survival", Immunity, vol. 14, pp. 801-811 (2001).

Kalish et al, Alopecia Areata: Autoimmunity—The Evidence is Compelling, J. Investig. Dermatol., Symp. Proc., vol. 8, pp. 164-167 (2003).

Kaya et al, "Cutting Edge: A Critical Role for IL-10 in Induction of Nasal Tolerance in Experimental Autoimmune Myocarditis", J. Immunol., vol. 168, pp. 1552-1556 (2002).

Kim et al, "Ligation of FeγRII (CD32) Pivotally Regulates Survival of Human Eosinophils", J. Immunol., vol. 162, pp. 4253-4259 (1999).

Kita et al, "Does IgE Bind to and Activate Eosinophils from Patients with Alelrgy?", J. Immunol., vol. 162, pp. 6901-6911 (1999).

Kohm et al, "Cutting Edge: CD4+ CD25+ Regulatory T cells Suppress Antigen-Specific Autoreactive Immune Responses and Central Nervous System Inflammation During Active Experimental Autoimmune Encephalomyelitis", J. Immunol., vol. 169, pp. 4712-4716 (2002).

Kossard, "Postmenopausal Frontal Fibrosing Alopecia", Arch. Dermatol., vol. 130, pp. 770-774 (1994).

Lafont et al, "Production of TNF-α by Human Vγ9Vδ2 T Cells Via Engagement of FcγRIIA, the Low Affinity Type 3 Receptor for the Fc Portion of IgG, Expressed upon TCR Activation by Nonpeptidic Antigen", J. Immunol., vol. 166, pp. 7190-7199 (2001).

Laliotou et al, "Interphotoreceptor Retinoid Binding Protein is a Potent Tolerogen in Lewis Rat: Suppression of Experimental Autoimmune Uveoretinitis is Retinal Antigen Specific", Br. J. Ophthalmol., vol. 81, pp. 61-67 (1997).

Laliotou et al, "Modulating Phenotype and Cytokine Production of Leucocytic Retinal Infiltrate in Experimental Autoimmune Uveoretinitis Following Intranasal Tolerance Induction with Retinal Antigens", Br. J. Ophthalmol., vol. 83, pp. 478-485 (1999).

Laliotou et al, "Intranasal Administration of Retinal Antigens Induces Transient T cell Activation and Apoptosis within Drainage Lymph Nodes but not Spleen", J. Autoimmun., vol. 12, pp. 145-155 (1999).

Lanier, "Natural Killer Cells: From No Receptors to Too Many", Immunity, vol. 6, pp. 371-378 (1997).

Lanier et al, "Association of DAP12 with Activating CD94/NKG2C NK Cell Receptors", Immunity, vol. 8, No. 6, pp. 693-701 (1998).

Lanier et al, "Immunoreceptor DAP12 Bearing a Tyrosine-Based Activation Motif is Involved in Activating NK Cells", Nature, vol. 391, No. 6668, pp. 703-707 (1998).

Lanier et al, "The ITAM-bearing Transmembrane adaptor DAP12 in lymphoid and myeloid cell function", Immunology Today, vol. 21, No. 12, pp. 611-614 (2000).

Lesourne, Renaud, et al., *J. Biol. Chem.*, 276(9):6327-6336, Mar. 2, 2001. "Insufficient phosphorylation prevents Fc☐RIIB from recruiting the SH2 domain-containing protein-tyrosine phosphates SHP-1."

Levy, "The House that JAK/STAT Built", Cytokine & Growth Factor Reviews, vol. 8, Issue 1, pp. 81-90 (1997).

Liversidge et al, "Nitric Oxide Mediates Apoptosis Through Formation of Peroxynitrite and Fas/Fas-Ligand Interactions in Experimental Autoimmune Uveitis", Am. J. Path., vol. 160, pp. 905-916 (2002).

Long, "Regulation of Immune Responses Through Inhibitory Receptors", Ann. Rev. Immunol., vol. 17, pp. 875-904 (1999).

Lopez-Botet et al, "Natural Killer Cell Activation and Inhibition by Receptors for MHC Class I", Curr. Opin. Immunol., vol. 11, No. 3, pp. 301-307 (1999).

Lu-Kuo, Jennifer M., et al., *J. Biol. Chem.*, 274(9):5791-5796, Feb. 26, 1999. "gp49B1 Inhibits IgE-initiated mast cell activation through immunoreceptor tyrosine-based inhibitory motifs, recruitment of src homology 2 domain-containing phosphatase-1, and suppression of early and late calcium mobilization".

Luross et al, "The genetic and immunopathological process underlying collagen-induced arthritis", Immunology, vol. 103, pp. 407-416 (2001).

Mahe et al, J"Androgenetic Alopecia and microinflammation", Int. J. Dermatol., vol. 39, pp. 576-584 (2000).

Malbec, Odile, et al., *J. Immunol.*, 162(8):4424-4429, Apr. 15, 1999. "Negative regulation of c-kit mediated cell proliferation by FcγRIIB."

Malbec, Odile, et al., *J. Immunol.*, 160(4):1647-1658, Feb. 15, 1998. "Fc☐0 Receptor I-associated lyn-dependent phosphorylation of Fc☐receptor IIB during negative regulation of mast cell activation".

Marone et al, "Human mast cells and basophils in HIV-1 infection", Trends in Immunology, vol. 22, No. 5, pp. 229-232 (2001).

Marra et al, Definition: vh96g05.y1 Barstead Mouse Myotubes MPLRB5 Mus Musculus cDNA clone Image: 902168 5', mRNA sequence, Database EMBL Sequences, Online!, Accession No. AI613766 (Apr. 26, 1999).

Massey et al, "Intranasal Peptide-Induced Peripheral Tolerance: The Role of IL-10 in Regulatory T Cell Function Within the Context of Experimental Autoimmune Encephalomyelitis", Vet. Immunol., Immunopathol, vol. 87, pp. 357-372 (2002).

McCaughan et al, "Characterization of the Human Homolog of the Rat MRC OX-2 Membrane Glycoprotein", Immunogenetics, vol. 25, pp. 329-335 (1987).

McElwee et al, "In Vivo Depletion of CD8+ T Cells Restores Hair Growth in the DEBR Model for Alopecia Areata", br. J. Dermatol., vol. 135, pp. 211-217 (1996).

McElwee et al, "Alopecia Areata—Animal Models", Clin. Exp. Dermatol., vol. 27, pp. 410-417 (2002).

Merchant et al, "The LMP2A ITAm Is Essential for Providing B Cells with Development and Survival Signals in Vivo", J. Biol. Chem., vol. 74, pp. 9115-9123 (2000).

Meyaard, Linde, et al., *Immunity*, 7(2):283-290, Aug. 1997 "LAIR-1, a novel inhibitory receptor expressed on human mononuclear leukocytes."

Millar et al, Molecular Mechanisms Regulating Hair Follicle Development, J. Invest. Dermatol., vol. 118, pp. 216-225 (2002).

Morgan et al, "An Investigation of Apoptosis in Androgenetic Alopecia", Ann. Clin. Lab Sci., vol. 33, pp. 107-112 (2003).

Moriyama et al, "Role of Aspartic Acid 814 in the Function and Expression of c-kit Receptor Tyrosine Kinase", J. Biol. Chem., vol. 271, pp. 3347-3350 (1996).

Muchamuel et al, "IL-13 Protects Mice from Lipopolysaccharide-Induced Lethal Endotoxemia", The Journal of Immunology, vol. 158, pp. 2898-2903 (1997).

Muller-Rover et al, "A Comprehensive Guide for the Accurate Classification of Murine Hair Follicles in Distinct Hair Cycle Stages", J. Invest. Dermatol., vol. 117, pp. 3-15 (2001).

Nathan et al, "Putting the Brakes on Innate Immunity: A Regulatory Role for CD200?", Nature Immunology, vol. 2, pp. 17-19 (2001).

Newton-Nash et al, "A New role for Platelet-Endothelial Cell Adhesion Molecule-1 (CD31): Inhibition of TCR-Mediated Signal Transduction", J. Immunol., vol. 163, pp. 682-688 (1999).

Nieman et al, "Designer Skin: Lineage Commitment in Postnatal Epidermis", Trends Bell Biol., vol. 12, pp. 185-192 (2002).

Nussenblatt et al, "Inhibition of S-Antigen Induced Experimental Autoimmune Uveoretinitis by Oral Induction of Tolerance with S-Antigen", J. Immunol., vol. 144, No. 5, pp. 1689-1695 (1990).

Okayama et al, "A comparison of Mediators Released or Generated by IFN-γ-Treated Human Mast Cells Following Aggregation of FcγRI or FIεRI", Journal of Immunology, vol. 166, pp. 4705-4712 (2001).

Ott et al, "Activating and Inhibitory Signaling in Mast Cells: New Opportunities for Therapeutic Intervention?" The Journal of Allergy and Clinical Immunology, vol. 106, No. 3, pp. 429-440 (2000).

Pan et al, "CD72-Deficient Mice Reveal nonredundant Roles of CD72 in B Cell Development and Activiation", Immunity, vol. 11, pp. 495-506 (1999).

Pandey et al, "Identification of a Novel Immunoreceptor Tyrosine-Based Activation Motif-Containing Molecule, STAM2, by Mass Spectrometry and Its Involvement in Growth Factor and Cytokine Receptor Signaling Pathways", J. Biol. Chem., vol. 275, pp. 38633-38639 (2000).

Paus et al, "Expression of Classical and Non-Classical MHC Class I Antigens in Murine Hair Follicles", Br. J. Dermatol., vol. 131, pp. 177-183 (1994).

Perez-Villar, Juan J., et al., *Mol. Cell. Biol.*, 19(4):2903-2912, Apr. 1999. "CD5 negatively regulates the T-cell antigen receptor signal transduction pathway: involvement of SH2-containing phosphotyrosine phospatase SHP-1."

Perret et al, "Immunohistochemical Analysis of T-cell Subsets in the Peribulbar and Intrabulbar Infiltrates of Alopecia Areata", Acta Derm. Venereol., vol. 64, pp. 26-30 (1984).

Pierard-Franchimont et al, "Massive Lymphocyte-Mediated Apoptosis During the Early Stage of Pseudopelade", Dermatologica, vol. 172, pp. 254-257 (1986).

Prakken et al, "Inhibition of Adjuvant-Induced Arthritis by Interleukin-10-Driven Regulatory Cells Induced Via Nasal Administration of a Peptide Analog of an Arthritis-Related Heat-Shock Protein 60 T Cell Epitope", Arthritis Rheum., vol. 46, No. 7, pp. 1937-1946 (2002).

Preston et al, "The leukocyte/neuron cell surface antigen OX2 binds to a ligand on macrophages", European Journal of Immunology, vol. 27, pp. 1911-1918 (1997).

Price, "Therapy of Alopecia Areata: on the Cusp and in the Future", JID Symp., Proc., vol. 8, pp. 207-211 (2003).

Propst et al, "Proinflammatory and Th2-Derived Cytokines Modulate CD40-Mediated Expression of Inflammatory Mediators in Airway Epithelia: Implications for the Role of Epithelial CD40 in Airway Inflammation", J. Immunol., vol. 165, pp. 2214-2221 (2000).

Ranki et al, "Immunohistochemical and Electron Microscopic Characterization of the Cellular Infiltrate in Alopecia (Areata, Totalis, and Universalis)", J. Invest. Dermatol., vol. 83, pp. 7-11 (1984).

Raso, Vic, et al., *J. Biol. Chem.*, 272(44):27623-27628, Oct. 31, 1997. "Intracellular targeting with low pH-triggered bispecific antibodies".

Ravetch et al, "Immune Inhibitory Receptors", Science, vol. 290, pp. 84-89 (2000).
Ribatti et al, "The Role of Mast Cells in Tumor Angiogenesis", British Journal of Haematology, vol. 115, pp. 514-521 (2001).
Sathish et al, "Constitutive Association of SHP-1 with Leukocyte-Associated Ig-Like Receptor-1 in Human T Cells", J. Immunology, vol. 166, pp. 1763-1770 (2001).
Robertson et al, "Retinal Microenvironment Controls Resident and Infiltrating Macrophage Function during Uveoretinitis" Invest. Ophthalmol. Vis. Sci., vol. 43, pp. 2250-2257 (2002).
Roncarolo et al, "Type 1 T Regulatory Cells", Immunol. Rev., vol. 182, pp. 68-79 (2001).
Safavi et al, "Incidence of Alopecia Areata in Olmsted County, Minnesota, 1975 through 1989", Mayo Clin. Proc., vol. 70, pp. 628-633 (1995).
Sarmay, Gabriella, et al., J. Biol. Chem., 271(48):30499-30504, Nov. 29, 1996. "Human type II Fc receptors inhibit B cell activation by interacting with the $p21^{ras}$-dependent pathway."
Sato et al, "CD22 is Both a Positive and Negative Regulator of B Lymphocyte Antigen Receptor Signal Transduction: Altered Signaling in CD22-Deficient Mice", Immunity, vol. 5, pp. 551-562 (1996).
Segal, David M., et al., J. Immunol. Methods, 248(1-2):1-6, Feb. 1, 2001. "Introduction: bispecific antibodies".
Shi et al, "Nasal Tolerance in Experimental Autoimmune Myasthenia Gravis (EAMG): Induction of Protective Tolerance in Primed Animals", Clin. Exp. Immunol., vol. 111, pp. 506-512 (1998).
Shi et al, "Mechanisms of Nasal Tolerance Induction in Experimental Autoimmune Myasthenia Gravis: Identification of Regulatory Cells", J. Immunol., vol. 162, pp. 5757-5763 (1999).
Silvennoinen et al, "Cytokine Receptor Signal Transduction Through Jak Tyrosine Kinases and Stat Transcription Factors", APMIS, vol. 105, No. 7, pp. 497-509 (1997).
Sinclair, Why So Many Coinhibitory Receptors?, Scan. J. Immunol., vol. 50, pp. 10-13 (1999).
Slominski et al, "Hair cycle-dependent production of ACTH in mouse skin", Biochem. Biophys. Acta, vol. 1448, pp. 147-152 (1998).
Smith et al, "The Challenges of Genome Sequence Annotation orThe Devil is in the Details", Nature Biotechnology, vol. 15, pp. 1222-1223 (1997).
Stuart et al, "Editorial: Monkeying Around with Collagen Autoimmunity and Arthritis", Lab. Invest. vol. 54, No. 1, pp. 1-3 (1986).
Sperling, "Scarring Alopecia and the Dermatophathologist", J. Cutaneous Pathol., vol. 28, pp. 333-342 (2001).
Stein et al, "Interleukin 4 Potently Enhances Murine Macrophage Mannose Receptor Activity: A Marker of Alternative Immunologic Macrophage Activation", J. Exp. Med., vol. 176, pp. 287-292 (1992).
Stumbles et al, "Resting Respiratory Tract Dendritic Cells Preferentially Stimulate T Helper Cell Type 2 (Th2) Responses and Require Obligatory Cytokine Signals for Induction of Th1 Immunity", J. Exp. Med., vol. 188, No. 11, pp. 2019-2031 (1998).
Stumpo et al, "Alternative Activation of Macrophage by IL-10", Pathobiology, vol. 67, pp. 245-248 (1999).
Sullivan et al, "Acquired Scalp Alopecia. Part I: A Review", Australas J. Dermatol., vol. 39, pp. 207-219 (1998).
Sundberg et al, "Asebia-2J ($Scd1^{ab21}$): A New Allele and a Model for Scarring Alopecia", Am. J. Pathol., vol. 156, No. 6, pp. 2067-2075 (2000).
Supplementary Partial European Search Report issued in corresponding EP 02801055 (Sep. 13, 2004).
Suri-Payer et al, "CD4+ CD25+ T Cells Inhibit Both the Induction and Effector Function of Autoreactive T Cells and Represent a Unique Lineage of Immunoregulatory Cells", J. Imrnunol., vol. 160, pp. 1212-1218 (1998).
Svensson et al, "B Cell-Deficient Mice Do Not Develop Type II Collagen-Induced Arthritis (CIA)", Clin. Exp. Immunol., vol. 111, pp. 521-526 (1998).
Thomas et al.; U.S. Appl. No. 09/810,883; Publication No. US 2001/0053770 A1.
Thornton et al, "Suppressor Effector Function of $CD4^+CD25^+$Immunoregulatory T Cells Is Antigen Nonspecific", J. Immunol., vol. 164, pp. 183-190 (2000).
Tomasello et al, "Association of Signal-Regulatory Proteins β with KARAP/DAP-12", Eur. J. Immunol., vol. 30, pp. 2147-2156 (2000).
Thurau et al, "Oral Tolerance for Treating Uveitis—New Hope for an Old Immunological Mechanism", Progress in Retinal and Eye Research, vol. 21, pp. 577-589 (2002).
Tivol et al, "Costimulation and Autoimmunity", Curr. Opin. Immunol., vol. 8, pp. 822-830 (1996).
Tobin et al, "Cell Degeneration in Alopecia Areata: An Ultrastructural Study", Am. J. Dermatopathol., vol. 13, pp. 248-256 (1991).
Tobin, "Morphological Analysis of Hair Follicles in Alopecia Areata", Microsc. Res. Tech., vol. 38, pp. 443-451 (1997).
Toyoda et al, "Expression of Neuropeptide-Degrading Enzymes in Alopecia Areata: An Immunohistochemical Study", Br. J. Dermatol., vol. 144, pp. 46-54 (2002).
Traunecker et al, "Biospecific Single Chain Molecules (Janusins) Target Cytotoxic Lymphocytes on Hiv Infected Cells", EMBO J., vol. 10, pp. 3655-3659 (1991).
Trueb et al, "Lichen Planopilaris Unter Dem Bild einer Postmenopausalen Frontalen Fibrosierenden Alopezie (Kossard)", Hautarzt, vol. 49, pp. 388-391 (1998).
Tsokos et al, "Immune Cell Signaling in Lupus", Curr. Opin. Rheumatol., vol. 12, pp. 355-363 (2000).
Tsuboi et al, "Characterization of Infiltrating T Cells in Human Scalp Explants From Alopecia Areata to SCID Nude Mice: Possible Role of the Disappearance of CD8+ T Lymphocytes in the Process of Hair Regrowth", J. Dermatol., vol. 26, pp. 797-802 (1999).
Uhrberg et al, "The Repertoire of Killer Cell Ig-Like Receptor and CD94:NKG2A Receptors in T Cells: Clones Sharing Identifical αβ TCR Rearrangement Express Highly Diverse Killer Cell Ig-Like Receptor Patterns", J. Immunol., vol. 166, pp. 3923-3932 (2001).
Ujike et al, "Modulation of Immunoglobulin (Ig)E-Mediated Systemic Anaphylaxis by Low-Affinity Fc Receptors for IgG", J. Exp. Med., vol. 189, pp. 1573-1579 (1999).
Van de Loo et al, "An Oleate 12-Hydroxylase from Icinus Comunis L. is a Fatty Acyl Saturase Homolog", Proc. Natl. Acad. Sci. USA, vol. 92, No. 15, pp. 6743-6747 (1995).
Vasioukhin et al, "The Magical Touch: Genome Targeting in Epidermal Stem Cells Induced by Tamoxifen Application to Mouse Skin", Proc. Natl. Acad. Sci. USA, vol. 96, pp. 8551-8556 (1999).
Von Andrian et al, "T-Cell Function and Migration: Two Sides of the Same Coin", New Engl. J. Med., vol. 343, pp. 1020-1034 (2000).
Wang et al, "Mouse Natural Killer Cells Express gp49B1, a Structural Homologue of Human Killer Inhibitory Receptors", Immunol., vol. 158, pp. 13-17 (1997).
Welker et al, "Hair Cycle-Dependent Changes in the Gene Expression and Protein Content of Transforming Factor β1 and β3 in Murine Skin", Arch. Dermatol. Res., vol. 289, pp. 554-557 (1997).
Whiting, "Histopathologic Features of Alopecia Areata", Arch. Dermatol., vol. 139, pp. 1555-1559 (2003).
Wisniewski, et al, "A 62-kilodalton Tyrosine Phosphoprotein Constitutively Present in Primary Chronic Phase Chronic Myelogenous Leukemia Enriched Lineage Negative Blast Populations", Leukemia, vol. 8, No. 4, pp. 688-693 (1994).
Wright et al. 2003 "Characterization of the CD200 Receptor Family in Mice and Humans and Their Interactions with CD200"; J. Immunol. 171:3034-3046.
Wright et al, "Lymphoid/Neuronal Cell Surface OX2 Glycoprotein Recognizes a Novel Receptor on Macrophages Implicated in the control of their Function", Immunity, vol. 13, pp. 233-242 (2000).
Wright et al, "The unusual distribution of the neuronal/lymphoid cell surface CD200 (OX2) glycoprotein is conserved in humans", Immunology, vol. 102, pp. 173-179 (2001).
Young et al, "Differential Expression of Leukocyte Receptor Complex-Encloded Ig-Like Receptors Correlates with the Transition from Effector to Memory CTL", J. Immunol., vol. 166, pp. 3933-3941 (2001).
Yuasa et al, "Deletion of Fcγ Receptor $II^B$ Renders H-2b Mice Susceptible to Collagen-Induced Arthritis", J. Exp. Med., vol. 189, pp. 187-194 (1999).

Zheng et al, "Expression of the Platelet Receptor GPVI Confers Signaling via the Fc Receptor γ-Chain in Response to the Snake Venom Convulxin but Not to Collagen" J. Biol. Chem., vol. 276, pp. 12999-13006 (2001).

Zinkernagel et al, "Fibrosing Alopecia in a Pattern Distribution: Patterned Lichen Planopilaris or Androgenetic Alopecia with a Lichenoid tissue Reaction Pattern?", Arch. Dermatol., vol. 136, pp. 205-211 (2000).

Zöller, et al, "Transient CD44 Variant Isoform Expression and Reduction in CD4+/CD25+ Regulatory T cells in C3H/HeJ Mice with Alopecia Areata", J. Invest. Dermatol., vol. 118, pp. 983-992 (2002).

SEQUENCE LISTING

<160> NUMBER OF SEQ ID NOS: 5

<210> SEQ ID NO 1
<211> LENGTH: 16
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: "X" can be any amino acid residue
<220> FEATURE:
<221> NAME/KEY: MISC_FEATURE
<222> LOCATION: (6)..(11)
<223> OTHER INFORMATION: "X" can be any amino acid residue
<220> FEATURE:
<221> NAME/KEY: MISC_FEATURE
<222> LOCATION: (13)..(14)
<223> OTHER INFORMATION: "X" can be any amino acid residue

<400> SEQUENCE: 1

Tyr Xaa Xaa Leu Ile Xaa Xaa Xaa Xaa Xaa Xaa Tyr Xaa Xaa Leu Ile
1               5                   10                  15

<210> SEQ ID NO 2
<211> LENGTH: 17
<212> TYPE: PRT
<213> ORGANISM: Homo sapiens
<220> FEATURE:
<221> NAME/KEY: MISC_FEATURE
<222> LOCATION: (2)..(3)
<223> OTHER INFORMATION: "X" can be any amino acid residue
<220> FEATURE:
<221> NAME/KEY: MISC_FEATURE
<222> LOCATION: (6)..(12)
<223> OTHER INFORMATION: "X" can be any amino acid residue
<220> FEATURE:
<221> NAME/KEY: MISC_FEATURE
<222> LOCATION: (14)..(15)
<223> OTHER INFORMATION: "X" can be any amino acid residue

<400> SEQUENCE: 2

Tyr Xaa Xaa Leu Ile Xaa Xaa Xaa Xaa Xaa Xaa Xaa Tyr Xaa Xaa Leu
1               5                   10                  15

Ile

<210> SEQ ID NO 3
<211> LENGTH: 18
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: "X" can be any amino acid residue
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (6)..(13)
<223> OTHER INFORMATION: "X" can be any amino acid residue
<220> FEATURE:
<221> NAME/KEY: MISC_FEATURE
<222> LOCATION: (15)..(16)
<223> OTHER INFORMATION: "X" can be any amino acid residue

<400> SEQUENCE: 3

Tyr Xaa Xaa Leu Ile Xaa Xaa Xaa Xaa Xaa Xaa Xaa Xaa Tyr Xaa Xaa
1               5                   10                  15

Leu Ile

```
<210> SEQ ID NO 4
<211> LENGTH: 9
<212> TYPE: PRT
<213> ORGANISM: Homo sapiens
<220> FEATURE:
<221> NAME/KEY: MISC_FEATURE
<222> LOCATION: (4)..(4)
<223> OTHER INFORMATION: "X" can be any amino acid residue
<220> FEATURE:
<221> NAME/KEY: MISC_FEATURE
<222> LOCATION: (6)..(7)
<223> OTHER INFORMATION: "X" can be any amino acid residue

<400> SEQUENCE: 4

Ile Val Leu Xaa Tyr Xaa Xaa Leu Val
1               5

<210> SEQ ID NO 5
<211> LENGTH: 7
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: "X" can be any amino acid; motif pattern can
      repeat 3-5 times

<400> SEQUENCE: 5

Leu Xaa Xaa Xaa Xaa Xaa Xaa
1               5
```

USE OF BISPECIFIC ANTIBODIES TO REGULATE IMMUNE RESPONSES

CROSS-REFERENCE TO RELATED APPLICATION

This application is a continuation of U.S. Ser. No. 10/270,084 filed Oct. 11, 2002 which claims the benefit of U.S. Provisional Patent Application No. 60/329,182, filed Oct. 12, 2001, the disclosures of which are hereby incorporated by reference in their entirety.

FIELD OF THE INVENTION

The present invention relates to methods for controlling the activity, development, differentiation, proliferation rate, and migration, of cells of the mammalian immune system. In particular, the invention relates to methods for cross-linking an inhibitory receptor with an activating receptor using a bispecific antibody. The cross-linking results in the inhibition of the activating receptor.

BACKGROUND OF THE INVENTION

The immune system is used to combat bacteria, viruses, and foreign multicellular organisms, as well as cancerous cells. Immune responses are provided by cells of the bone marrow, spleen, and other tissues. Unfortunately, improper regulation of the immune system can result in a number of disorders or pathological conditions. These disorders or conditions include chronic inflammation, autoimmune disease, and undesired allergic reactions to foreign particles or foreign tissues.

Cells of the immune system possess many types of membrane-bound proteins that serve as receptors. The ligands for these receptors may be small molecules, proteins, e.g., cytokines or chemokines, or membrane-bound proteins residing on a separate cell. The occupation of a receptor by its ligand, binding of a receptor by a soluble antibody, cross-linking of like-receptors to each other, and cross-linking of unlike receptors to each other, can result in changes in cellular activity. Some of these events result in "cell activation," while other events result in "cell inhibition."

Studies of immune cells and their activation or inhibition have related to: Recruitment of enzymes to the plasma membrane; recruitment of enzymes to "lipid rafts" in the cell membrane (Yang and Reinherz, J. Biol. Chem. 2766, 18775 (2001)), and recruitment of membrane-bound receptors to the plasma membrane. A lipid raft is a region of the plasma membrane with reduced fluidity of the lipid molecules. Cell activation or inhibition also relates to changes in phosphorylation state of receptors; changes in the proliferative state of the cell; calcium fluxes; changes in genetic expression; changes in secretion or in degranulation; differentiation of the cell; changes in the proliferative rate of the cell; changes in cell migration; and changes in chemotaxis. Cell activation may also include the reversal of T cell anergy (see, e.g., Lin, et al., J. Biol. Chem. 273, 19914 (1998); and Sunder-Plassman and Reinherz, J. Biol. Chem. 273, 24249 (1998)).

The question of whether a signaling event, which results in any of the above changes, is activating or inhibiting can be determined on an individual basis. For example, if occupation of an unidentified receptor results in an increases of genetic expression of cytokine mRNA, secretion (or degranulation), release of inflammatory cytokines, phagocytic or lytic activity, the unidentified receptor may be termed an activating receptor. Similarly, if occupation of an unidentified receptor inhibits activity dependent on a known activating receptor, then that unidentified receptor may be termed an inhibiting receptor.

The determination of whether a receptor is activating or inhibiting may be predicted by the polypeptide sequence of the receptor, where the receptor is a protein. Attention has focused on two different motifs: ITIM and ITAM. ITIM stands for immunoreceptor tyrosine-based inhibition motif, while ITAM means immunoreceptor tyrosine-based activation motif. A number of polypeptide receptors bearing one or more ITIM motifs in the cytosolic region of the receptor have been found to be inhibiting, whereas a number of polypeptide receptors bearing one or more ITAM sequences in the cytosolic region have been found to be activating.

The cross-linking of an inhibiting receptor with an activating receptor may result in inhibition of the activating receptor. Traditionally, cross-linking involves the use of three components, where these components are added an incubation medium containing cultured cells, such as cultured T cells or mast cells. Generally, two of these components are antibodies, where each antibody recognizes a different antigen on the cell surface. A third component is often a third independent antibody which recognizes the constant region of the first two antibodies.

A multi-component cross-linking system allows for efficient and controlled studies in conducting research experiments with cultured cells. However, a multi-component cross-linking system is not a practical method for pharmaceutical intervention or drug therapy. One disadvantage is that cross-linking using a three-component system requires four different binding reactions. A second disadvantage is the use of three antibodies to cross-link receptors is therapeutically not feasible.

The present invention addresses these problems by providing one bispecific antibody, which is capable of binding and physiologically affecting an activating receptor and inhibiting receptor on a cell of the immune system.

SUMMARY OF THE INVENTION

The present invention provides a method for using a bispecific antibody to reduce the activity of a cell or of an activating receptor, wherein said bispecific antibody binds to: (a) an activating receptor; and (b) an inhibiting receptor. In further embodiments, the inhibiting receptor contains an ITIM motif, and may be selected from the group consisting of: FcγRIIB, LAIR-1, KIR, OX2R, OX2Ra, DSP-1, CD5, MAFA, CTLA-4, HM18, Ly49, and gp49B1. In another embodiment, the activating receptor contains an ITAM motif and may be selected from the group consisting of FcεRI, FcγRIII, FcγRIIA, FcγRIIC, T-cell receptor, TREM-1, TREM-2, CD28, CD3, CD2, and DAP-12. In another embodiment, the activating receptor is FcεRI and the inhibiting receptor is OX2Ra.

The present invention contemplates that the bispecific antibody comprises a chemical linking agent that is covalently incorporated into the bispecific antibody. In another embodiment, the bispecific antibody is a single polypeptide chain antibody or is humanized.

In a further embodiment, the bispecific antibody is administered in conjunction with an agent that stimulates expression of an inhibiting receptor or an activating receptor. This agent is selected from the group consisting of granulocyte colony stimulating factor and interferon-γ. It is also contemplated that the bispecific antibody is administered in conjunction with a therapeutic selected from the group consisting of an antiinflammatory agent, a chemotherapeutic agent, an immunosuppressive agent, and an anti-malarial agent. In a further embodiment, the antiinflammatory agent is selected from the group consisting of corticosteroids, glucocorticoids, soluble tumor necrosis factor receptor, and antibodies against tumor necrosis factor. In still another embodiment, the chemotherapeutic agent is selected from the group consisting of methotrexate, vincristine, and cyclophosphamide.

The present invention provides a composition comprising the bispecific antibody of claim 1 in conjunction with an acceptable carrier. In another embodiment the bispecific antibody is administered. The method of claim 1, in vivo or to cultured cells.

The present invention provides a kit comprising the bispecific antibody in a compartment; and instructions for use.

DETAILED DESCRIPTION

As used herein, including the appended claims, the singular forms of words such as "a," "an," and "the" include their corresponding plural references unless the context clearly dictates otherwise.

Definitions

An "antibody" or "antibody molecule" generally consists of two heavy chains and two light chains, where usually each light chain is linked to a heavy chain by a disulfide bond, and where usually the two heavy chains are linked together by a disulfide bond (Brody, Analyt. Biochem. 247, 247 (1997)). Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 more amino acids. (Abbas, et al., Cellular and Molecular Immunology, 4th ed., W.B. Saunders Co., Phila. (2000), pp. 41-62.

A "bispecific antibody" refers to vinding fragments from two different antibodies, humanized binding fragments from two different antibodies, or peptide mimetics of binding fragments from two different antibodies. Each binding fragment recognizes a different receptor, e.g., an inhibiting receptor and an activating receptor. Bispecific antibodies normally exhibit specific binding to two separate antigens.

The term "cocktail" refers to a solution from which aliquots may be withdrawn, and then transferred to a reaction mixture or cell incubation mixture. In some cases, the cocktail may supply a mixture of different antibodies, for the purpose of initiating a cross-linking reaction. In other cases, the cocktail may supply a mixture of ancillary compounds to the reaction mixture, such as a combination of protease inhibitors. Cocktails are pre-mixed combinations of reagents that allow the transfer of reagents to be effected more rapidly and more accurately.

"Epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics.

The term "expression of receptor" may refer to the rate of transcription (mRNA synthesis), rate of translation (polypeptide synthesis), rate of transfer of a receptor polypeptide from an intracellular compartment to an extracellular compartment, or to the proportion of receptor polypeptide occurring in as: [extracellular]/[intracellular+extracellular] compartment.

The term "receptor" refers to a class of proteins, including the membrane-bound proteins of a cell that can be associated with a biological ligand or an analogue thereof, such as a hormone, a cytokine, an antibody, a membrane-bound protein of another cell, or a ligand bound to the membrane of another cell. The membrane-bound receptor may reside on the plasma membrane, or may reside on an intracellular vesicle, destined for eventual insertion in the plasma membrane. A ligand may serve as an agonist or an antagonist of the receptor (Goodman, et al. (1990) Goodman & Gilman's: The Pharmacological Bases of Therapeutics (8th ed.) Pergamon Press, Tarrytown, N.Y.). The association between the ligand and receptor may be temporary or permanent, and it may involve a non-covalent linkage or a covalent linkage. Many receptors are used to control cell behavior or cell-signaling events. Where the association of a ligand with a receptor provokes an increase in a cellular event, the receptor is called an "activating" receptor. Where the association of a ligand with a receptor provokes a decrease in a cellular event, the receptor may be called "inhibiting." In the cases of some receptors, various ligands can provoke either the activation or the inhibition of the receptor, and here the receptor may be termed "activating" or "inhibiting," depending on which ligand is used most often in the physiological situation. A protein or other macromolecule may be called a receptor because it binds a naturally occurring ligand, but also because it binds a synthetic or non-physiological ligand, such as a drug or experimental probe.

The term "activating receptor" is most accurately used to refer to a single polypeptide chain comprising a ligand-binding region and a cytosolic signaling region, or a complex of polypeptides, comprising a ligand-binding polypeptide and a cytosolic signaling polypeptide. However, in the interest of facilitating discussions of cell biology or biochemistry, any one of the polypeptides of a multi-polypeptide activating receptor may be termed an "activating receptor." An inhibitory receptor may exert its inhibitory effect on a number of different activating receptors, that is, not solely on one type of activating receptor.

A receptor can be both activating and inhibiting, where the activating or inhibiting effect depends on the physiology of the cell. For example, CD22 (a protein of human and mouse B cells) contains both ITAM (activating motif) and ITIM (inhibiting motif) motifs, and can exert an activating or inhibiting effect on the B cell receptor, depending on the physiology and surroundings of the B cell (Gergely, et al., Immunology Letters 68, 3 (1999); Sato, et al., Immunity 5, 551 (1996)). The question of whether any given receptor is inhibiting or activating may depend on the ligand, for example, one type of mitogen versus another type of mitogen (Sato, et al., Immunity 5, 551 (1996)).

Where a polypeptide receptor used in cell activation does not contain an activating domain, but is bound to a second polypeptide that does contain an activating domain, it is acceptable to refer to each of the following three entities as an "activating receptor": (1) The polypeptide receptor not containing an activating domain; (2) The polypeptide containing the activating domain; and (3) The entire complex of the above-mentioned two polypeptides.

The term "receptor" is broadly defined to include membrane-bound or membrane-associated macromolecules that may be targeted by a pharmaceutical agent, but are not necessarily the target of a physiological ligand. The term "receptor" also includes macromolecules that are covalently or non-covalently associated with the outside surface of the plasma membrane, and not necessarily inserted into the phospholipid bilayer of the plasma membrane.

"Motif" refers to a sequence of amino acids within a polypeptide, where that sequence confers specific properties to that polypeptide.

General

The present invention provides a bispecific antibody that can bind specifically to two separate receptors of a cell. In the field of immunology, two types of receptors bearin two types of motifs are encountered in a number of membrane-bound receptors of white blood cells. These the receptors and their respective motifs are called the ITAM and ITIM. The consensus ITAM sequence is $YxxL/Ix_{6-8}YxxL/I$, where (Y) may be phosphorylated resulting in a change in signaling properties of the activating receptor and/or the accessory protein. The ITAM motif may occur within an activating receptor itself, or within an accessory protein that binds to the activating receptor, thus conferring activating properties to the activating receptor. ITAM receptors as described below The ITIM motif is defined by the consensus sequence I/V/LxYxxL/V in the cytoplasmic domain where (Y) can be phosphorylated, resulting in the ability of the polypeptide bearing the ITIM motif to recruit various enzymes, where the enzymes aid in relaying an inhibitory signal to the cell (Sathish, et al., J. Immunol. 166, 1763 (2001)).

Examples of inhibitory receptors include, e.g., FcγRIIB, LAIR, FDF03, KIR, gp49B, ILT25, PIR-B, Ly49, CTLA4, DSP-1, CD200Ra/OXRa, CD94/NKG2A, NKG2B-E, PECAM-1, CD5, CD22, CD72, PIR1, SIRPα, HM18, LRC, ILT, KIR, LIR, MIR, and MAFA (see, e.g., Long (1999) *Ann. Rev. Immunol.* 17:875; Lanier (1997) *Immunity* 6:371; Newton-Nash and Newman (1999) *J. Immunol.* 163:682; Azzam, et al. (2001) *J. Immunol.* 166:5464; Perez-Villar, et al. (1999) *J. Immunol.* 19:2903; Sinclair (1999) *Scan. J. Immunol.* 50:10; Pan, et al. (1999) *Immunity* 11:495; Tomasello, et al. (2000) *Eur. J. Immunol.* 30:2147; Arm, et al. (1997) *J. Immunol.* 159:2342; Borges, et al. (1997) *J. Immunol.* 159:5192; Young, et al. (2001) *J. Immunol.* 166:3933; Lafont, et al (2001) *J. Immunol.* 166:7190; Uhrberg, et al. (2001) *J. Immunol.* 166:3923; Zlot, et al. WO 01/36463; Guthman, et al. (1995) *Proc. Natl. Acad. Sci.* 92:9397; and Blaser, et al. (1998) *J. Immunol.* 161:6451).

Activating receptors include, e.g., CD3, CD2, CD10, CD161, DAP-12, KAR, KARAP, FcεRI, FcεRII, FcγRIIA, FcγRIIC, FcγRIII/CD16, Trem-1, Trem-2, CD28, p44, p46, B cell receptor, LMP2A, STAM, STAM-2, GPVI, and CD40 (See, e.g., Azzoni, et al. (1998) *J. Immunol.* 161:3493; Kita, et al. (1999) *J. Immunol.* 162:6901; Merchant, et al. (2000) *J. Biol. Chem.* 74:9115; Pandey, et al. (2000) *J. Biol. Chem.* 275:38633; Meng, et al. (2001) *J. Biol Chem.* 276:12999; Propst, et al. (2000) *J. Immunol.* 165:2214).

Cross-Linking Studies

Cross-linking KIR (inhibiting) with FcεRI (activating). The following study, involving a mast cell-like cell line transfected with KIR revealed that cross-linking of KIR (inhibiting) to FcεRI (activating) results in the cell inhibition. The cell that was studied was an artificial construct. Cross-linking of FcεRI to FcεRI (to itself) resulted in cell activation. A mixed situation, where FcεRI was cross-linked to FcεRI (to itself), and where FcεRI was also cross-linking of KIR, resulted in inhibition of cell activation. This mixed situation demonstrates the inhibitory effect of KIR. The following control experiment was also conducted. A mixed situation where FcεRI was cross-linked to FcεRI (to itself) and where KIR was cross linked to KIR, did not result in inhibitory effects (Blery, et al. J. Biol. Chem. 272, 8989 (1997)).

Details of the cross-linking reactions are as follows. In a first step, FcεRI was tagged by adding mouse IgE. Here, FcεRI became bound by IgE. In a second step, one mouse IgE/FcεRI complex was cross-linked to another mouse IgE/FcεRI complex with donkey anti-mouse F(ab)'$_2$. The scenario described so far results only in cell activation.

In a third experimental step, KIR (inhibiting) was cross-linked to a mouse IgE/FcεRI complex. Here, KIR was first tagged with mouse anti-human GL183 F(ab)'$_2$. Then a mouse anti-human GL183 F(ab)'$_2$/KIR complex was cross-linked to mouse IgE/FcεRI complex with a bridging antibody (donkey anti-mouse DAM F(ab)'$_2$). The result of this third step, was an inhibition of cell activation (Blery, et al., J. Biol. Chem. 272, 8989 (1997)).

Cross-linking KIR (inhibiting) with CD25/CD3ζ (activating). The cross-linking of KIR can result in an inhibition of CD25/CD3ζ-dependent cell activity (Blery, et al., J. Biol. Chem. 272, 8989 (1997)). CD25/CD3ζ is a chimeric molecule composed of CD25 ecto- and transmembrane domains fused to CD3ζ (Donnadieu, et al., Proc. Natl. Acad. Sci. 269, 32828 (1994)). Cross-linking of KIR with CD25/CD3ζ can inhibit CD25/CD3ζ-mediated cell activation. Stimulation of CD25/CD3ζ alone can result in calcium fluxes and in serotonin release. However, simultaneous cross-linking of KIR (inhibitory receptor) with CD25/CD3ζ (activating receptor) can reduce or prevent the CD25/CD3ζ-mediated calcium flux and serotonin release. The cross-linking cocktail contained IgE (targets CD25/CD3ζ), GL183 (targets KIR), and donkey anti-rat Ig F(ab)'$_2$ (Blery, et al., J. Biol. Chem. 272, 8989 (1997)).

Cross-linking Gp49B1 (inhibiting) with FcεRI (activating). Gp49B1 is a protein of mouse cells, not human cells. Gp49B1 occurs on mouse mast cells, as well as on mouse NK cells stimulated with IL-2 (Wang, et al., J. Immunol. 158, 13 (1997)). The physiological ligand for gp49B1 is MHC class I molecules. Gp49B1 contains an ITIM motif. Gp49B1 shares a 35% amino acid identity with the human protein, KIR. A human homologue of gp49B1, called HM18, occurs on human mast cells, human monocytes, and human NK cells.

Cross linking of gp49B1 and FcεRI on mouse mast cells was studied using the cross-linking cocktail comprising rat IgE, rat IgM anti-gp49B1, anti-gp49B1, and F(ab')$_2$ mouse anti-rat IgG (Lu-Kuo, et al., J. Biol. Chem. 274, 5791 (1999)). The cross-linking of gp49B1 with FcεRI inhibited cell activation, as measured by monitoring the association of SHP-1 (a phosphatase) with gp49B1, by measuring calcium fluxes, and by measuring enzyme secretion.

Cross-linking FcγRIIB (inhibiting) with FcεRI (activating). The following study, involving a mast cell-like cell line with transfected FcγRIIB demonstrated that cross-linking of FcγRIIB (inhibiting) to FcεRI (activating) results in the cell inhibition. The cell line that was used an artificial construct. Cross-linking of FcεRI to FcεRI (to itself) results in cell activation. A mixed situation, where FcεRI was cross-linked to FcεRI (to itself), and where FcεRI was cross-linking of FcγRIIB, results in reduced cell activation. This mixed situation demonstrates the inhibitory effect of FcγRIIB (Blery, et al., J. Biol. Chem. 272, 8989 (1997)).

Cross-linking was effected as follows. In a first step, FcεRI was tagged by adding mouse IgE. Here, FcεRI becomes bound by IgE. In a second step, one mouse IgE/FcεRI complex is cross-linked to another mouse IgE/FcεRI complex with donkey anti-mouse F(ab)'$_2$. The scenario described so far results only in cell activation.

In a third experimental step, FcγRIIB (inhibiting) was cross-linked to a mouse IgE/FcεRI complex. Here, FcγRIIB was first tagged with 2.4G2, resulting in a 2.4G2/FcγRIIB complex. Then a rat 2.4G2/FcγRIIB complex was cross-linked to mouse IgE/FcεRI complex with a bridging antibody (TNP-F(ab)'$_2$MAR). In other words, TNP-F(ab)'$_2$MAR is used to cross-link mouse anti-TNP IgE and rat anti-FcγRII 2.4G2. The result of this third step is inhibition of cell activation (Blery. et al., J. Biol. Chem. 272, 8989 (1997)).

The cross-linking FcγRIIB and FcεRI has been characterized by a number of other investigators. In one study, cross-linking was by a cocktail containing IgE and F(ab')$_2$ fragments of RAM Ig (Malbec, et al., J. Immunol. 160, 1647 (1998)). In a similar study, cross-linking was by a cocktail containing IgE anti-DNP, 2.4G2 F(ab')$_2$, and TNP-MAR F(ab')$_2$ (Lesourne, et al., J. Biol. Chem. 276, 6327 (2001)).

Human basophils have also been used to illustrate the effects of cross-linking FcγRIIB (inhibiting) with FcεRI (activating). These studies revealed that cross-linking has an inhibitory effect (FIG. 1A in Daeron, et al., Immunity 3, 635 (1995)).

Cross-linking FDF03 (inhibiting) with FcγRII (activating). FDF03 is a human membrane-bound protein found in monocytes, macrophages, granulocytes, and monocyte-derived dendritic cells. FDF03 contains an ITIM motif in its cytoplasmic region and thus may be abbreviated as FDF03-ITIM.

FcγRII in humans occurs in three forms, where one is an inhibitory receptor and two are activating receptors. FcγRIIA and FcγRIIC are activating, and contain an ITAM motif, and thus may be represented as FcγRIIA-ITAM and FcγRIIC-ITAM. In contrast, FcγRIIB is inhibiting, and may be represented as FcγRIIB-ITIM (Kim, et al., J. Immunol. 162, 4253 (1999)). The study reported below concerned one of the activating forms of FcγRII, where the exact form was not stated.

An artificial construct was made involving FDF03 transfected in U937 cells. FDF03 and were FcγRII (activating) were cross-linked to each other with a cross-linking cocktail. The cross-linking cocktail contained mABIV.3 (binds FcγRII), mAB36H2 (binds FDF03), and goat F(ab')$_2$anti-mouse Ig (cross-links the above two antibody/antigen complexes). Adding anti-FcγRII alone to the cells provoked calcium flux. However, adding the entire cross-linking cocktail did not result in the calcium flux. The conclusion is that the cross-linking of FDF03 to FcγRII results in inhibition of the FcγRII-mediated cellular activation (Fournier, et al., J. Immunol. 165, 1197 (2000)).

Cross-linking LAIR-1 (inhibiting) with FcγRII (activating). LAIR-1 contains an ITIM motif, and hence may be abbreviated as LAIR-1-ITIM. LAIR-1 (inhibiting) and FcγRII (activating) and were cross-linked to each other with a cross-linking cocktail. The cross-linking cocktail contained mAbIV.3 (binds FcγRII), mAb DX26 (binds LAIR-1), and goat F(ab')$_2$anti-mouse Ig. Adding anti-FcγRII alone to the cells provoked calcium flux. However, adding the entire cross-linking cocktail did not result in the calcium flux. The conclusion is that the cross-linking of LAIR-1 to FcγRII inhibits the FcγRII-mediated cellular activation that would be seen with use of anti-FcγRII alone (Fournier, et al., 165, 1197 (2000)). An effect, in addition to prevention of calcium flux, is the inhibition of differentiation of the cells. Where the cells are monocytes, cross-linking of FcγRII with LAIR-1 inhibited the differentiation of the monocytes to dendritic cells (Fournier, et al., 165, 1197 (2000)).

Cross-linking FcγRIIB (inhibiting) with B cell receptor (activating). FcγRIIB (also called CD32B) is a membrane-bound protein of B cells. B cells proliferate and secrete antibodies in response to exposure to foreign antigen. The antibodies secreted by the B cell exert a feedback effect on the B cell, where this negative feedback effect is by means of contact of the antibody with FcγRIIb and the B cell receptor. Stimulation of FcγRIIb (inhibiting) by pharmaceutical means is expected to be useful in disease states where B cell activity results in harm. These include autoimmune diseases, such as rheumatoid arthritis. Studies with mice revealed that B cell deficient mice do not develop experimental arthritis (Svensson, et al., Clin. Exp. Immunol. 111, 521 (1998)). Consistent with this finding is that mice deficient in FcγRIIb have increased arthritis (apparently because FcγRIIb is not present, and thus cannot exert its inhibitory effect) (Yuasa, et al., J. Exp. Med. 189, 187 (1999)).

It might also be noted that FcγRIIB is present not only on B cells, but also on mast cells and macrophages, where the FcγRIIB also exerts an inhibitory effect (Daeron, et al., 3, 635 (1995); Ujike, et al., J. Exp. Med. 189, 1573 (1999)).

FcγRIIB bears an ITIM motif in its cytoplasmic region. FcγRIIB occurs in two forms in humans, namely, FcγRIIB1 and FcγRIIB2 (Bruhns, et al., J. Biol. Chem. 275, 37357 (2000)). The B cell receptor is a complex of mIg (this binds the antigen), Ig-α (part of signaling unit), and Ig-β (part of signaling unit).

Ig-α and Ig-β each contain an ITAM motif. Cross-linking of one B cell receptor to another B cell receptor by polyvalent antigen results in cell activation. However, cross-linking of B cell receptor to FcγRIIB is inhibitory, as mentioned above. Cross-linking (co-ligation) of these two receptors results in the phosphorylation of a tyrosine residue in the ITIM motif, resulting the conversion of FcγRIIb-ITIM to FcγRIIb-ITIM-phosphate (Gergely, et al., Immunology Letters 68, 3 (1999); Coggeshall, Curr. Opinion Immunol. 10, 306 (1998); Sarmay, et al., J. Biol. Chem. 271, 30499 (1996)).

Experimental cross-linking of the two receptors can be accomplished by adding to cells: (1) Intact IgG anti-IgM; (2) Aggregated IgG plus anti-Ig; or (3) Adding anti-FcγRBII (anti-CD32BI) followed by biotinylated anti-mouse IgG and biotinylated anti-human Ig plus avidin (Sarmay, et al. (1996)).

The cross linking of FcγRIIB (inhibiting) with CD3ε (activating), a component of the T cell receptor, was shown in the cultured cell lines, RMA cells and 2B4 cells. This work demonstrated that cross linking FcγRIIB (inhibiting) with CD3ε (activating) resulted in inhibition of CD3ε-mediated activation (FIG. 2C in Daeron, et al., Immunity 3, 635 (1995)).

Cross-linking FcγRIIB (inhibiting) with FcγRIIA (activating). Studies with transfected cells demonstrated that cross linking FcγRIIB (inhibiting) with FcγRIIA (activating) resulted in inhibition of FcγRIIA-mediated activation (FIG. 1C in Daeron, et al., Immunity 3, 635 (1995)).

Cross-linking FcγRIIB (inhibiting) with c-kit (activating). c-Kit is a membrane bound protein that functions as an activating receptor. c-Kit does not contain an ITAM motif. The protein occurs on mast cells, where it functions in innate immune mechanisms, in contrast to FcεRI of mast cells, which functions in adaptive immune mechanisms (Lu-Kuo, et al., J. Biol. Chem. 275, 6022 (2000)). c-Kit belongs to the colony-stimulating factor/platelet-derived growth factor receptor subfamily, where the aforementioned proteins belong to the RTK family (receptor tyrosine kinase family) (Moriyama, et al., J. Biol. Chem. 271, 3347 (1996)).

Studies with mast cells revealed that cross-linking FcγRIIB (inhibiting) with c-kit (activating) inhibited c-kit-mediated cell proliferation. Cross-linking was accomplished by adding ACK2-biotin plus anti-biotin (Malbec, et al., J. Immunol. 162, 4424 (1999)). Details of the study were as follows. In control studies, cells were pre-treated with 2.4G2 (an antibody), an antibody that blocks the binding site of FcγRIIB, rendering FcγRIIB non-functional as an inactivating receptor. Cells were pre-treated with the blocking antibody, subsequent addition of ACK2-biotin plus anti-biotin induced cells to proliferate (FIG. 4 of Malbec, et al., J. Immunol. 162, 4424 (1999)).

Cross-linking CD5 (inhibiting) with CD3 (activating). CD5 is a membrane-bound protein found on T cells and on subpopulations of B cells. CD5 belongs to the scavenger receptor cysteine-rich (SRCR) family. This family includes CD5, CD6, WC1, M130, Spα, Pema-STEG, Ebnerin, CPR-ductin, hensin, and gallbladder mucin (Perez-Villar, Mol. Cell. Biol. 19, 2903 (1999)). The cytoplasmic domain of CD5 contains ITAM-like sequences and ITIM-like sequences. Studies with T cells illustrated the inhibitory properties of CD5, as they related to the T cell receptor or, more specifically, to the CD3 component of the T cell receptor.

Cross-linking of CD5 (inhibiting) with T cell receptor (activating) was accomplished with a cross-linking cocktail containing biotinylated anti-CD3, biotinylated anti-CD5, and avidin. Cross-linking resulted in decreases in T cell receptor-dependent cell activation, as shown by measurements of $Ca^{2+}$ levels (Perez-Villar, Mol. Cell. Biol. 19, 2903 (1999)).

Production of Bispecific Antibodies

The invention provides for bispecific antibodies in which two different antigen-binding sites are incorporated into a single molecule. Bispecific antibodies may be prepared by chemical cross-linking (Brennan, et al., Science 229, 81 (1985); Raso, et al., J. Biol. Chem. 272, 27623 (1997)), disulfide exchange, production of hybrid-hybridomas (quadromas), by transcription and translation to produce a single polypeptide chain embodying a bispecific antibody, or by transcription and translation to produce more than one polypeptide chain that can associate covalently to produce a bispecific antibody. The contemplated bispecific antibody can also be made entirely by chemical synthesis. The bispecific antibody may comprise two different variable regions, two different constant regions, a variable region and a constant region, or other variations.

An example of use of transcription/translation to produce a single polypeptide chain bispecific antibody is as follows. Certain animals (camels; llamas; dromedaries) produce heavy chain antibodies, where there is no associated light chain. These antibodies have a single variable region, which can bind to antigen. Recombinant bispecific antibodies comprising two variable regions (from two different heavy chain antibodies) plus a linker region (from llama upper hinge) have been produced. The resulting complex ($VH_1$-LH-$VH_2$) can be expressed in bacteria (Conrath, et al., J. Biol. Chem. 276, 7346 (2001)). Humanized counterparts of the bispecific antibodies based on camel heavy chain antibodies are contemplated.

Single chain variable fragments have been connected to each other to form a bispecific antibody by various techniques: cross-linking C-terminal cysteine residues, adding naturally associating helices from a four-helix bundle, adding leucine zippers, adding a CH3 domain with either a knob or hole at the interacting surfaces, or by connecting CH1 and CL domains to the respective scFV fragments (Conrath, et al., J. Biol. Chem. 276, 7346 (2001)).

Chemically constructed bispecific antibodies may be prepared by chemically cross-linking heterologous Fab or F(ab')$_2$ fragments by means of chemicals such as heterobifunctional reagent succinimidyl-3-(2-pyridyldithiol)-propionate (SPDP, Pierce Chemicals, Rockford, Ill.). The Fab and F(ab')$_2$ fragments can be obtained from intact antibody by digesting it with papain or pepsin, respectively (Karpovsky, et al., J. Exp. Med. 160, 1686 (1984); Titus, et al., J. Immunol., (38, 4018 (1987)).

Oligopeptides and polypeptides may be used for linking two different antibodies or antibody chains together. Oligo- and polypeptides may be synthesized by solution phase or by solid phase techniques. These include processes such as are described in Stewart and Young, Solid Phase Peptide Synthesis, Pierce Chemical Co., Rockford, Ill. (1984); Bodanszky, The Principles of Peptide Synthesis, 2nd ed., Springer, New York (1993); and Molina, et al., Pept. Res. 9, 151 (1996)). For example, an azide process, an acid chloride process, an acid anhydride process, a mixed anhydride process, an active ester process (for example, p-nitrophenyl ester, N-hydroxy-succinimide ester, or cyanomethyl ester), a carbodiimidazole process, an oxidative-reductive process, or a dicyclohexylcarbodiimide (DCCD)/additive process can be used.

Quadromas may be constructed by fusing hybridomas that secrete two different types of antibodies against two different antigens (Milstein and Cuello, Nature 305, 537(1983); Kurokawa et al., Biotechnology 7, 1163 (1989)). Bispecific antibodies can also be prepared by the transfectoma method (Morrison, Science 229, 1202 (1985)). The invention additionally encompasses bispecific antibody structures produced within recombinant microbial hosts as described in PCT application WO 93/11161 and Holliger, et al., Proc. Natl. Acad. Sci. USA, 90, 6444 (1993). Also included are bispecific linear molecules, such as the so-called "Janusin" structures described by Traunecker, et al., EMBO J. 10, 3655 (1991). This can be accomplished by genetically removing the stop codons at the end of a gene encoding a monomeric single-chain antigen-binding protein and inserting a linker and a gene encoding a second single-chain antigen-binding protein (WO 93/11161).

The antigen recognition site of most antibodies is comprised of the variable region of the heavy chain and the variable region of the light chain. Both of these variable regions are in close contact with each other, and form the antigen-recognition site. Single chain antibodies contain two variable regions on one polypeptide chain, where one variable region is equivalent to that of a conventional light chain, and the other variable region is equivalent to a conventional heavy chain. The design of single chain antibodies includes attention to the linking polypeptide region, which connects the two variable regions. Single chain antibodies can be synthesized by chemical means, or by means of translation using a single open reading frame. Details on the synthesis of single chain antibodies are described in U.S. Pat. No. 4,946,778 issued to Ladner, et al.

In a further approach, bispecific antibodies are formed by linking component antibodies to leucine zipper peptides (Kostelny et al., J. Immunol. 148, 1547 (1992); de Kruif and Logtenberg, J. Biol. Chem. 271, 7630 (1996)). Leucine zippers have the general structural formula (Leucine-$X_1$-$X_2$-$X_3$-$X_4$-$X_5$-$X_6$)$_n$, where X may be any of the conventional 20 amino acids (Creighton. Proteins, Structures and Molecular Principles, W. H. Freeman and Company, New York (1984)), but are most likely to be amino acids with high α-helix forming potential, for example, alanine, valine, aspartic acid, glutamic acid, and lysine (Richardson and Richardson, Science 240, 1648 (1988)), and n may be 3 or greater, although typically n is 4 or 5. The leucine zipper occurs in a variety of eukaryotic DNA-binding proteins, such as GCN4, C/EBP, c-fos gene product (Fos), c-jun gene product (Jun), and c-myc gene product. In these proteins, the leucine zipper creates a dimerization interface wherein proteins containing leucine zippers may form stable homodimers and/or heterodimers.

The leucine zippers for use in the present invention preferably have pairwise affinity. Pairwise affinity is defined as the capacity for one species of leucine zipper, for example, the Fos leucine zipper, to predominantly form heterodimers with another species of leucine zipper, for example, the Jun leucine zipper, such that heterodimer formation is preferred over homodimer formation when two species of leucine zipper are present in sufficient concentrations (Schuemann, et al., Nucleic Acids Res. 19, 739 (1991)). Thus, predominant formation of heterodimers leads to a dimer population that is typically 50 to 75 percent, preferentially 75 to 85 percent, and most preferably more than 85 percent heterodimers. When amino-termini of the synthetic peptides each include a cysteine residue to permit intermolecular disulfide bonding, heterodimer formation occurs to the substantial exclusion of homodimerization.

In the formation of bispecific antibodies, binding fragments of the component antibodies are fused in-frame to first and second leucine zippers. Suitable binding fragments including Fv, Fab, Fab', or the heavy chain. The zippers can be linked to the heavy or light chain of the antibody binding fragment and are usually linked to the C-terminal end. If a constant region or a portion of a constant region is present, the leucine zipper is preferably linked to the constant region or portion thereof. For example, in a Fab'-leucine zipper fusion, the zipper is usually fused to the C-terminal end of the hinge. The inclusion of leucine zippers fused to the respective component antibody fragments promotes formation of heterodimeric fragments by annealing of the zippers. When the component antibodies include portions of constant regions (e.g., Fab' fragments), the annealing of zippers also serves to bring the constant regions into proximity, thereby promoting bonding of constant regions (e.g., in a F(ab'), fragment). Typical human constant regions bond by the formation of two disulfide bonds between hinge regions of the respective chains. This bonding can be strengthened by engineering additional cysteine residue(s) into the respective hinge regions allowing formation of additional disulfide bonds.

Leucine zippers linked to antibody binding fragments can be produced in various ways. For example, polynucleotide sequences encoding a fusion protein comprising a leucine zipper can be expressed by acellular host or in vitro translation system. Alternatively, leucine zippers and/or antibody binding fragments can be produced separately, either by chemical peptide synthesis, by expression of polynucleotide sequences encoding the desired polypeptides, or by cleavage from other proteins containing leucine zippers, antibodies, or macromolecular species, and subsequent purification. Such purified polypeptides can be linked by peptide bonds, with or without intervening spacer amino acid sequences, or by non-peptide covalent bonds, with or without intervening spacer molecules, the spacer molecules being either amino acids or other non-amino acid chemical structures. Regardless of the method or type of linkage, such linkage can be reversible. For example, a chemically labile bond, either peptidyl or otherwise, can be cleaved spontaneously or upon treatment with heat, electromagnetic radiation, proteases, or chemical agents. Two examples of such reversible linkage are: (1) a linkage comprising a Asn-Gly peptide bond which can be cleaved by hydroxylamine, and (2) a disulfide bond linkage which can be cleaved by reducing agents.

Component antibody fragment-leucine zippers fusion proteins can be annealed by co-expressing both fusion proteins in the same cell line. Alternatively, the fusion proteins can be expressed in separate cell lines and mixed in vitro. If the component antibody fragments include portions of a constant region (e.g., Fab' fragments), the leucine zippers can be cleaved after annealing has occurred. The component antibodies remain linked in the bispecific antibody via the constant regions.

Monoclonal antibodies (MAbs) may be obtained by various techniques familiar to those skilled in the art. Briefly, spleen cells from an animal immunized with a desired antigen are immortalized, commonly by fusion with a myeloma cell (Kohler and Milstein, Eur. J. Immunol. 6, 511(1976)). Alternative methods of immortalization include transformation with Epstein Barr Virus (EBV), oncogenes, or retroviruses, or other methods well known in the art. Colonies arising from single immortalized cells are screened for production of antibodies of the desired specificity and affinity for the antigen. Yield of the MAbs produced by such cells may be enhanced by various techniques, including injection into the peritoneal cavity of a vertebrate host.

Humanization of an antibody derived from an animal can result in decreased immunogenicity in the human body, increased half-life, and less activation of resting T cells. Where a desired antibody has been discovered or produced in a mouse, the antibody may be humanized by grafting complementarity-determining regions of mouse antibody into human antibody sequences. In other words, the constant regions of the mouse antibody are replaced with human constant regions. An additional useful alteration is to introduce mutations in the Fc region that result in lesser binding of the antibody to the human Fc receptor (Carpenter, et al., J. Immunol. 165, 6205 (2000); He, et al, J Immunol. 160, 1029 (1998)).

The following reveals a number of contemplated embodiments of the bispecific antibody. In these embodiments, the term "anti-" refers to a polypeptide, polypeptide region, or polypeptide fragment that specifically binds to the indicated target. It is contemplated the certain embodiments may be modified by a bridging region or hinge region, a signal sequence, by a glycosyl, phosphoryl, sulfate, or acetyl group, by a carboxylated glutamate residue (Gla), by disulfide bonds, by a purification tag such as oligo-histidine or glutathione S-transferase, by a peptide bond cleavage, by a detectable ligand, such as a fluorescent tag or radioactive tag ($^{35}S$, $^{3}H$, $^{14}C$, $^{33}P$, $^{32}P$, $^{125}I$), by biotinylation, or by an agent intended to promote stability in the body, such as polyethyleneglycol (PEG; pegylated antibody).

The contemplated bispecific antibody may be comprised of anti-KIR and anti-CD2, anti-KIR and anti-CD3, anti-KIR and anti-DAP-12, anti-KIR and anti-KAR, anti-KIR and anti-KARAP, anti-KIR and anti-FcεRI, anti-KIR and anti-FcγRIIA, anti-KIR and anti-FcγRIIC, anti-KIR and anti-FcγRIII, anti-KIR and anti-Trem-1, anti-KIR and anti-CD28, anti-KIR and anti-T cell receptor, or anti-KIR and anti-B cell receptor.

It is further contemplated that the contemplated bispecific antibody may be comprised of anti-FcγRIIB and anti-CD2, anti-FcγRIIB and anti-CD3, anti-FcγRIIB and anti-DAP-12, anti-FcγRIIB and anti-KAR, anti-FcγRIIB and anti-KARAP, anti-FcγRIIB and anti-FcεRI, anti-FcγRIIB and anti-FcγRIIA, anti-FcγRIIB and anti-FcγRIIC, anti-FcγRIIB and anti-FcγRIII, anti-FcγRIIB and anti-Trem-1, anti-FcγRIIB and anti-CD28, anti-FcγRIIB and anti-T cell receptor, or anti-FcγRIIB and anti-B cell receptor.

Uses

Bispecific antibodies of the present invention are useful in the treatment or diagnosis of immune disorders, abnormal cell proliferation, etc. Such disorder include diseases involving cells which bear activating and/or inhibitory receptors, e.g., IgE-dependent conditions, inflammatory conditions of the skin or mucosa, autoimmune conditions, immune disorders of the nervous and muscle systems, systemic inflammation, and transplant related immune diseases (see, e.g., Salvi and Babu (2000) New Engl. J. Med. 342:1292; Saini et al.

(1999) *J. Immunol.* 162:5624; Barnes (1999) *New Engl. J. Med.* 341:2006; Kita, et al. (1999) *J. Immunol.* 162:6901; Targan et al. (1997) *New Engl. J. Med.* 337:1029; Simpson, et al. (1998) *J. Exp. Med.* 187:1225; Tobert and Kupper (1999) *New Engl. J. Med.* 341:340; Davidson and Diamond (2001) *New Engl. J. Med.* 345:340; Rose and Mackay (eds.) *The Autoimmune Diseases*, 3$^{rd}$ ed., Academic Press, San Diego, Calif.; Falk (2000) *New Engl. J. Med.* 343:1182; Mills (1994) *New Engl. J. Med.* 33:1871; and Blazar et al. (1997) *Immunol. Revs.* 157:79)

Therapeutic Compositions and Administration of a Bispecific Antibody

Therapeutic formulations of bispecific antibodies are prepared for storage by mixing antibody having the desired degree of purity with optional physiologically acceptable carriers, excipients, or stabilizers (Gemmarp. Remington's Pharmaceutical Sciences, 20th ed., Phila. (2000)), in the form of lyophilized cake or aqueous solutions. Acceptable carriers, excipients or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, Pluronics or polyethylene glycol (PEG).

The bispecific antibody to be used for in vivo administration must be sterile. Sterilization can be accomplished by filtration through sterile filtration membranes, prior to or following lyophilization and reconstitution. The bispecific antibody ordinarily will be stored in lyophilized form or in solution. Therapeutic bispecific antibody compositions generally are placed into a container having a sterile access port, for example, an intravenous solution bag or vial having a stopper pierceable by a hypodermic injection needle.

The route of administration is in accord with known methods, e.g. injection or infusion by intravenous, intraperitoneal, intracerebral, intramuscular, intraocular, intraarterial, intracerebrospinal, or intralesional routes, or by sustained release systems.

Suitable examples of sustained-release preparations include semipermeable polymer matrices in the form of shaped articles, e.g. films, or microcapsules. Sustained release matrices include polyesters, hydrogels, polylactides (U.S. Pat. No. 3,773,919, EP 58,481), copolymers of L-glutamic acid and gamma ethyl-L-glutamate (Sidman, et al., Biopolymers, 22, 547 (1983)), poly(2-hydroxyethyl-methacrylate) (Langer, et al., J. Biomed. Mater. Res., 15, 167 (1981)); Langer, Chem. Tech., 12, 98 (1982)), ethylene vinyl acetate (Langer, et al., Chem. Tech., 12, 98 (1982)), or poly-D-(−)-3-hydroxybutyric acid (EP 133,988). Sustained-release bispecific antibody compositions also include liposomally entrapped antibody. Liposomes containing antibody can be prepared (Epstein et al., Proc. Natl. Acad. Sci. USA, 82, 3688 (1985); Hwang et al., Proc. Natl. Acad. Sci. USA, 77, 4030 (1980); EP 52,322; EP 36,676; EP 88,046; EP 143, 949; EP 142,641; U.S. Pat. No. 4,485,045; U.S. Pat. No. 4,544,545; EP 102,324). Ordinarily the liposomes are of the small (about 200-800 Angstroms) unilamellar type in which the lipid content is greater than about 30 mol. % cholesterol, the selected proportion being adjusted for the optimal antibody therapy.

The bispecific antibody can also be administered by inhalation. Commercially available nebulizers for liquid formulations, including jet nebulizers and ultrasonic nebulizers are useful for administration. Liquid formulations can be directly nebulized and lyophilized powder can be nebulized after reconstitution. Alternatively, a bispecific antibody can be aerosolized using a fluorocarbon formulation and a metered dose inhaler, or inhaled as a lyophilized and milled powder.

An "effective amount" of bispecific antibody to be employed therapeutically will depend, for example, upon the therapeutic objectives, the route of administration, the type of bispecific antibody employed, and the condition of the patient. Accordingly, it will be necessary for the therapist to titer the dosage and modify the route of administrations required to obtain the optimal therapeutic effect. Typically, the clinician will administer the bispecific antibody until a dosage is reached that achieves the desired effect. The progress of this therapy is easily monitored by conventional assays.

In the treatment and prevention of a disorder by a bispecific antibody, the antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the antibody, the particular type of antibody, the method of administration, the scheduling of administration, and other factors known to medical practitioners. The "therapeutically effective amount" of antibody to be administered will be governed by such considerations, and is the minimum amount necessary to prevent, ameliorate, or treat the inflammatory disorder.

Therapeutic Applications

This invention provides reagents and therapeutics of value for the treatment of diseases or pathological states involving cells of the immune system. The reagents comprise bispecific antibodies. The bispecific antibody comprises two different regions, each of which recognizes and binds to an antigen. Generally, the antigens occur as part membrane-bound proteins residing on or near the plasma membrane of immunological cells. Generally, the antigens are receptors, such as receptors for cytokines, receptors for antibodies (e.g., Fc receptors), or receptors for foreign antigens (T cell receptor) foreign antigens. Where the bispecific antibody simultaneously binds two different cell surface antigens, the two antigens may be tethered together, and the close proximity of the two antigens (the two receptors) may result in functional communication between the two receptors. Where tethering involves an activating receptor and an inhibiting receptor, the end result may be inhibition of the activating receptor with consequent inhibition of cell activity. Cell activity may be assessed by calcium flux, change in phosphorylation state of the cytoplasmic portions of the receptors, change in recruitment of intracellular proteins to either the activating or inhibiting receptor, and recruitment of enzymes or proteins to "rafts" in the cell membrane (Yang and Reinherz, J. Biol. Chem. 276, 18775 (2001)). Change in cell activity may also be assessed by the state of differentiation of the cell, the state of proliferation of the cell, or by the ability of a cell to lyse a target cell.

Administration of the Bispecific Antibody in Combination with a Therapeutic Agent It is contemplated to use the bispecific antibody in combination with a therapeutic agent. Some of these agents, along with specific diseases that respond to therapy with that agent, are as follows. Psoriasis may be treated with corticosteroids, methotrexate, cyclosporine, alefacept, and methoxsalen (psoralen) with ultraviolet light (Granstein, New Engl. J. Med. 345, 284 (2001)). Rheumatoid arthritis may be treated with glucocorticoids, prednisolone, hydroxychloroquine, and sulfasalazine (Kirwan, et al., New Engl. J. Med. 333, 142 (1995)). Rheumatoid arthritis may also be treated with antibodies against tumor necrosis factor-α (infliximab, CDP571, D2E7, CDP870) (Feldmann and Maini, Annu. Rev. Immunol. 19, 163 (2001), and soluble forms of tumor necrosis factor-α receptor (etanercept, lenercept, pegylated truncated p55 TNF-R) (Feldmann and Maini, Annu. Rev. Immunol. 19, 163 (2001); Pisetsky, New Engl. J. Med. 342, 810 (2000)). Crohn's diseases may be treated with prednisone, mercaptopurine, azathioprine, infliximab, methotrexate, budesonide, cyclosporine, 5-acetylsalicylic acid, and growth hormone (Sartor, New Engl. J. Med. 342, 1664 (2000)). Systemic lupus erythematosus may be treated with aspirin or other non-steroidal antiinflammatory therapeutics, hydroxychloroquine or other anti-malarial therapeutics, quinacrine, danzol, vincristine, and cyclophosphamide (Mills, New Engl. J. Med. 330, 1871 (1994)). Allergic asthma may be treated with anti-IgE, glucocorticoids, or $\beta_2$-adrenergic-receptor agonists (Salvi and Babu, New Engl. J. Med. 342, 1292 (2000)), budesonide (corticosteroid), terbutaline ($\beta_2$-agonist) (Haahtela, et al., New Engl. J. Med. 331, 700 (1994)). Agents aimed at B cell responses include cyclophosphamide, methotrexate, leflunomide, brequinar, and
15-deoxyspergualin (Auchincloss and Sachs, Ann. Rev. Immunol. 16, 433 (1998)). Antagonists of histidine receptors (e.g., $H_1$-receptors) are used for the treatment of a number of allergic disorders, including chronic urticaria (Greaves, New Engl. J. Med. 332, 1767 (1995)), allergic rhinitis, asthma, urticaria, atopic dermatitis, allergic rhinoconjunctivitis, anaphylaxis, and pruritis (Simons and Simons, New Engl. J. Med. 330, 1663 (1994)). These antagonists include fexofenadine (Kay, New Engl. J. Med. 344, 109 (2001)), terfenadine, astemizole, loratidine, cetirizine, acrivastine, levocabastine, azelastine, diphenhydramine, hydroxyzine, doxepin, triprolidine, and chlorpheniramine (Greaves, New Engl. J. Med. 332, 1767 (1995)).

It is contemplated to use the bispecific antibody in conjunction with an immunosuppressant, such as methotrexate, methylprednisolone, antilymphocyte globulin, antithymocyte globulin, cyclosporine, azathioprine, steroids, lymphoic irradiation (Kawauchi, et al., J. Thorac. Cardiovasc. Surg. 106, 779 (1993); Matsumiya, et al., Xenotransplantation 3, 76 (1996)), cyclophosphamide, mycophenolic acid (Thong, et al., Transplantation Proc. 28, 762 (1996)), tacrolimus (Ruzicka, et al., New Engl. J. Med. 337, 816 (1997)), rapamycin, FK506 (Blazar, et al., J. Immunol. 160, 5355 (1998)).

Kits and Quantitation

The bispecific antibody molecules of this invention are particularly useful in kits and assay methods. For example, these methods would also be applied to screening for binding and inhibitory activity on cultured cells. Several methods of automating assays have been developed in recent years so as to permit screening of tens of thousands of compounds per year (BIOMEK automated workstation, Beckman Instruments, Palo Alto, Calif., and Fodor, et al., Science 251, 767 (1991)). The latter describes means for testing binding by a plurality of defined polymers synthesized on a solid substrate. The development of suitable assays to screen for candidate target proteins can be greatly facilitated by the availability of large amounts of purified bispecific antibody such as is provided by this invention.

This invention also contemplates use of bispecific antibodies in a variety of diagnostic kits and methods for detecting cells of the immune system, where the activities of the cells may be inhibited by addition of the bispecific antibody. Typically the kit will have a compartment containing either a defined bispecific antibody which recognizes at least two epitopes, residing on one or more receptors. Compartments containing reagents, and instructions, will normally be provided.

Bispecific antibodies are useful in diagnostic applications to detect the presence of elevated levels of receptors, and in increased sensitivity of any given receptor to the receptor's ligand. Any increased sensitivity to the ligand, or to the bispecific antibody itself, will be predictive of the therapeutic outcome of in vivo use of the bispecific antibody. Increased sensitivity may be assessed by a biological assay, or by binding. Binding of the bispecific antibody to a patient's cells may be detected directly by using a radioactively labeled bispecific antibody, or indirectly by measuring the biological response. The introduction of labels into antibodies has been described (Harlow and Lane, Antibodies: A Laboratory Manual, Cold Spring Harbor (1988); Coligan, Current Protocols In Immunology Greene/Wiley, New York (1991 and periodic supplements)). Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins and binding fragments may be produced (Moore, et al. U.S. Pat. No. 4,642,334; Cabilly, U.S. Pat. No. 4,816,567).

Frequently, the reagents for diagnostic assays are supplied in kits, so as to optimize the sensitivity of the assay. For the subject invention, depending upon the nature of the assay, the protocol, and the label, either labeled or unlabeled bispecific antibody, provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent, and will contain instructions for proper use and disposal of reagents. Desirably, the reagents are provided as a dry lyophilized powder, where the reagents may be reconstituted in an aqueous medium having appropriate concentrations for performing the assay.

The aforementioned constituents of the diagnostic assays may be used without modification or may be modified in a variety of ways. For example, labeling may be achieved by covalently or non-covalently joining a moiety which directly or indirectly provides a detectable signal. Possibilities for direct labeling include label groups: radiolabels such as $^{125}I$, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

The methods for linking protein or fragments to various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Diagnostic kits which also test for the qualitative or quantitative presence of other markers are also contemplated. Diagnosis or prognosis may depend on the combination of multiple indications used as markers. Thus, kits may test for combinations of markers (Viallet, et al., Progress in Growth Factor Res. 1, 89 (1989)).

The invention will be better understood by reference to certain specific examples, which are intended for purposes of illustration and are not intended to be limited unless otherwise specified.

Examples

I. General Methods

Many of the standard methods below are described or referenced (Maniatis, et al., Molecular Cloning, A Laboratory Manual Cold Spring Harbor Laboratory, Cold Spring Harbor Press, NY (1982); Sambrook et al., Molecular Cloning: A Laboratory Manual (2d ed.) Vols. 1-3, CSH Press, NY (1989); Ausbel, et al., Current Protocols in Molecular Biology, Vol. 4, John Wiley and Sons, Inc., N.Y. (2000), and earlier volumes; Bonifacino, et al., Current Protocols in Cell Biology, Vol. 1, John Wiley and Sons, Inc., N.Y. (1998), and earlier volumes; Innis, et al., PCR Protocols: A Guide to Methods and Applications Academic Press, NY (1990)). Methods for protein purification include such methods as ammonium sulfate precipitation, column chromatography, electrophoresis, centrifugation, crystallization, and others (Deutscher (1990) "Guide to Protein Purification," Methods in Enzymology vol. 182, and other volumes in this series; and manufacturer's literature on use of protein purification products, e.g., Pharmacia, Piscataway, N.J., or Bio-Rad, Hercules, Calif.). Standard immunological techniques are described (Coligan, et al., Current Protocols in Immunology, Vol. 4, John Wiley and Sons, Inc., N.Y. (2001), and earlier volumes; Hertzenberg, et al., Weir's Handbook of Experimental Immunology vols. 1-4, Blackwell Science (1996); Methods in Enzymology volumes. 70, 73, 74, 84, 92, 93, 108, 116, 121, 132, 150, 162, and 163; Paul, Fundamental Immunology, 3d ed., Raven Press, N.Y (1993)).

II. Bispecific Antibody Recognizing KIR (Inhibiting) and FcγRIIIA (=CD16) (Activating) of the NK Cell, for Treatment of Asthma.

NK cells have been found to contribute to asthma. A study revealed that NK cells produce IL-5 which, in turn, contributes to eosinophil infiltration, and to the development of experimental asthma (Walker, et al., J. Immunol. 161, 1962 (1998)).

KIR occurs on NK cells and a subset of T-cells (CD8$^+$ memory T cells) (Vely, et al., J. Immunol. 166, 2487 (2001); Mingari, et al., Immunol. Today 19, 153 (1998)). FcγRIII (CD16) occurs on human NK cells (Palmieri, et al., J. Immunol. 162, 7181 (1999)). A bispecific reagent that binds KIR and FcγRIIIA is contemplated for the treatment of asthma.

CD94/NKG2-A occurs on human NK cells that binds CD94/NKG2-A and FcγRIIIA (Palmieri, et al., J. Immunol. 162, 7181 (1999)). A contemplated bispecific reagent that binds CD94/NKG2-A and FcγRIIIA is contemplated for the treatment of asthma.

LAIR-1 occurs on NK cells (Meyaard, et al., J. Immunol. 162, 5800 (1999)). A contemplated bispecific reagent that binds LAIR-1 and FcγRIIIA is contemplated for the treatment of asthma.

III. Bispecific Antibody Recognizing LAIR-1 (Inhibiting) and FcγRII (Activating) for Treatment of Rheumatoid Arthritis.

Cross-linking of LAIR-1 (inhibiting) to FcγRII (activating) results in inhibition of the FcγRII (activating)-mediated cellular activity (Fournier, et al., J. Immunol. 165, 1197 (2000)). The inhibited activities include calcium flux, as well as the differentiation of the monocytes to dendritic cells (Fournier, et al., J. Immunol. 165, 1197 (2000)).

LAIR-1 occurs on monocytes (Meyaard, et al., Immunity 7, 283 (1997)). FcγRIIA occurs on human monocytes (Cooney, et al., J. Immunol. 167, 844 (2001)). Hence, a disease state mediated by monocytes may be treated by the contemplated bispecific antibody, where the disease is initiated or exacerbated by stimulation of the FcγRIIA or FcγRIIB of the monocyte.

Rheumatoid arthritis is an autoimmune disease where the inflamed joint contains monocytes and monocyte-derived cytokines. Therapeutic use of antibodies directed against monocyte-derived cytokines, such as tumor necrosis factor-α, is an effective treatment of the disease (MacDonald, et al., J. Clin. Invest. 100, 2404 (1997)). There is some thought that monocyte-derived cytokines are the principal factors driving the local inflammatory response in rheumatoid arthritis (MacDonald, et al., J. Clin. Invest. 100, 2404 (1997)). A contemplated bispecific antibody reagent for cross-linking LAIR-1 and FcγRIIA or C is expected to be effective in treating rheumatoid arthritis.

IV. Treatment of Asthma by Cross-Linking FcγRIIB (Inhibiting) with FcγRIIA or C (Activating) of Eosinophils.

An antibody against FcγRII has been reported to activate human eosinophils. The antibody was considered to be activating because it inhibited eosinophil apoptosis and prolonged cell survival, and because the antibody in cross-linked form also prolonged survival of the eosinophils (Kim, et al., J. Immunol. 162, 4253 (1999)). FcγRIIB (inhibiting), FcγRIIA (activating), and FcγRIIC (activating) all occur in human eosinophils (Kim, et al., J. Immunol. 162, 4253 (1999)). Eosinophils contribute to the development of asthma (Busse and Lemanske, New Engl. J. Med. 344, 350 (2001); Chan-Yeung and Malo, New Engl. J. Med. 333, 107 (1995)).

V. Treatment of Allergy by Cross-Linking MAFA (Inhibiting) with FcεRI (Activating) of Mast Cells.

Mast cells contain MAFA (Guthmann, et al., Proc. Nat. Acad. Sci. USA 92, 9397 (1995)). Mast cells also contain FcεRI (Kalesnikoff, et al., Immunity 14, 801 (2001)). FcεRI, which is a high affinity receptor for IgE, is expressed on human mast cells. Activation of human mast cells through FcεRI is believed to be responsible for allergen-dependent allergic responses, where this interaction takes place in a Th2 environment (Okayama, et al., J. Immunol. 166, 4705 (2001)). Upon binding of antigen to IgE on the surface of mast cells, FcεRI becomes cross-linked, where cross-linking results in the secretion of histamine, cytokines, prostaglandins, and leukotrienes (Busse and Lemanske, New Engl. J. Med. 344, 350 (2001)). The contemplated bispecific antibody is expected to be useful for cross-linking MAFA and FcεRI, resulting in inhibition of mast cell activity, and treatment of the allergic responses.

A bispecific antibody reagent that binds FcγRIIB and FcεRI of mast cells (Hamanao, et al., J. Immunol. 164, 6113 (2000)) is also expected to be of use for treatment of allergic responses.

VI. Treating Sepsis by Cross-Linking FcγRIIB (Inhibiting) with CXCR1 (Activating) on Neutrophils.

The following discussion concerns IL-8 (ligand) and the IL-8 receptor (CXCR1). CXCR1 is an activating receptor of neutrophils. CXCR-1 binds IL-8 with high affinity, but binds other CXC chemokines with low affinity. It has been reported that neutrophils bear FcγRIIB, an inhibiting receptor (Ravetch and Clynes, Annu. Rev. Immunol. 16, 421 (1998); Long, Ann. Rev. Immunol. 17, 875 (1999)). In sepsis, neutrophils play the desirable role of defending against infection. However, the neutrophils also have the undesirable effect of contributing to multiple organ dysfunction syndrome and acute respiratory distress syndrome (Cummings, et al., J. Immunol. 162, 2341 (1999)). It is contemplated to use a bispecific antibody that binds to FcγRIIB (inactivating) and to CXCR1 (activating receptor) for the treatment of sepsis.

VII. Treatment of Systemic Lupus Erythematosis by a Bispecific Antibody that Cross-Links KIR (Inhibiting) and FcεRI (Activating).

Studies with cells bearing transfected receptors have demonstrated that cross-linking KIR (inhibiting) and FcεRI (activating) by an antibody cocktail can inhibit FcεRI-dependent cell activation (Blery, et al., J. Biol. Chem. 272, 8989 (1997)). KIR occurs on T cells (Bruhns, et al., J. Immunol. 162, 3168 (1999)). FcεRI also occurs on T cells (Petersson and Ivars, J. Immunol. 166, 6616 (2001)), where the following reports indicate that activation of T cell FcεRI may play a part in the ontology of lupus. T cells from the majority of patients with systemic lupus erythematosis have been found to show increased expression of FcεRIγ. In short, expression of FcεRIγ was about 4-fold higher in T cells of patients with the above disease, relative to that of T cells from normal subjects (Enyedy, et al., Arthritis Rheum. 44, 1114 (2001); Tsokos, et al., Curr. Opin. Rheumatol. 12, 355 (2000)). Antigen-receptor signaling via FcεRI has been found to be abnormal in lupus (Tsokos, et al., Curr. Opin. Rheumatol. 12, 355 (2000)). The above commentary applies to the γ-chain of FcεRI, which contains an ITAM motif (activating motif), and appears to have the ability to associate with the T cell receptor (Enyedy, et al., Arthritis Rheumatism 44, 1114 (2001)). In short, under certain conditions, the γ-chain of FcεRI may function not with FcεRI, but instead with T cell receptor. It is contemplated to use a bispecific antibody that binds to KIR (inactivating) and to FcεRI (activating) for the treatment of lupus.

VIII. Treatment of Rheumatoid Arthritis by a Bispecific Antibody that Cross-Links FcγRIIB (Inhibiting) and B Cell Receptor (Activating).

In rheumatoid arthritis, B cells accumulate in the joints, where these B cells produce rheumatoid factor. Rheumatoid factor consists of antibodies specific for the Fc portion of IgG, where the IgG is of the high affinity type. These high affinity rheumatoid factors contribute to the inflammation of rheumatoid arthritis (Kyburz, et al., J. Immunol. 163, 3116 (1999)). FcγRIIB and B cell receptor both occur on B cells. The major species of FcγR on the B cells appears to be FcγRIIB1 (Ashman, et al., J. Immunol. 157, 5 (1996)). Cross-linking of B cell receptor with FcγRIIB results in apoptosis and inhibition of B cell proliferation (Fong, et al., J. Immunol. 165, 4453 (2000)). The inhibitory effect of FcγRIIB, as it relates to arthritis, was demonstrated in studies with FcγRIIB-deficient mice. FcγRIIB-deficient mice have increased severity of collagen-induced arthritis (Yuasa, et al., J. Exp. Med. 189, 187 (1999)). Collagen-induced arthritis is a commonly used animal model of rheumatoid arthritis. It is contemplated to use a bispecific antibody that binds to FcγRIIB (inactivating) and to B cell receptor (activating) for the treatment of arthritis.

IX. Cross-Linking of CD5 (Inhibiting) and T Cell Receptor for Treatment of Psoriasis.

T cells have been identified as contributing to psoriasis, where stimulation of T cells appears to be by recognition of peptides by the T cell receptor (Costello, et al., J. Immunol. 166, 2878 (2001)). CD5 is an inhibitory receptor of T cells, as shown by studies using cross-linking cocktails comprised of biotinylated anti-CD5, biotinylated anti-CD3, and avidin (Perez-Villar, Mol. Cell. Biol. 19, 2903 (1999)). A bispecific antibody recognizing CD5 and T cell receptor is contemplated for the treatment of psoriasis. A bispecific antibody recognizing CD5 and CD3 (a component of T cell receptor) is also contemplated for the treatment of psoriasis.

X. Cross-Linking of LAIR-1 (Inhibiting) and T Cell Receptor for Treatment of Psoriasis.

T cells have been identified as contributing to psoriasis, where the stimulant of the T cells appears to be via recognition of peptides by the T cell receptor (Costello, et al., J. Immunol. 166, 2878 (2001)). LAIR-1 (inhibiting) has been identified on T cells (Meyaard, et al. J. Immunol. 162, 500 (1999). It is contemplated to use a bispecific antibody reagent that recognizes T cell receptor and LAIR-1 and T cell receptor for the treatment of psoriasis.

KIR (inhibiting) occurs on subsets of T cells (Vely, et al., J. Immunol. 166, 2487 (2001)). Hence, it is contemplated to use a bispecific antibody reagent that recognizes KIR and T cell receptor for the treatment of psoriasis.

XI. Cross-Linking of LAIR-1 (Inhibiting) and CD2 (Activating) for Treatment of Psoriasis.

CD2 is an activating receptor that is present on T cells (Wild, et al., J. Immunol. 163, 2064 (1999)). As mentioned above, CD2 functions in both T cell receptor-dependent and T cell receptor-independent pathways. The CD2 appears to play a major part in psoriasis, as drugs that target CD2 can be used to treat the disease (Ellis, et al., New Engl. J. Med. 345, 248 (2001)). LAIR-1 (inhibiting) occurs on T cells (Meyaard, et al., J. Immunol. 162, 5800 (1999)). It is contemplated to use a bispecific antibody reagent that recognizes both CD2 and LAIR-1 for the treatment of psoriasis.

KIR (inhibiting) occurs on subsets of T cells (Vely, et al., J. Immunol. 166, 2487 (2001); Uhrberg, et al., J. Immunol. 166, 3923 (2001)). It is contemplated to use a bispecific antibody reagent that recognizes both CD2 and KIR for the treatment of psoriasis.

NKG2A (inhibiting) can be found on subsets of T cells, where it occurs as a CD94/NKG2A complex (Uhrberg, et al., J. Immunol. 166, 3923 (2001)). It is contemplated to use a bispecific antibody reagent that recognizes both CD2 and NKG2A for the treatment of psoriasis.

XII. Stimulation and Assay of Degranulation.

Mast cells were plated in 96 well Falcon flat-bottom plates (Becton Dickinson Labware, Franklin Lakes, N.J.) and incubated in Roswell Park Memorial Institute (RPMI) media containing 1% bovine serum albumin (BSA). Cells were generally plated at $2 \times 10^5$ cells/well in the presence, e.g., of anti-muCD200R antibody (antibody DX109), isotype control antibody (rat $IgG_1$), a murine CD200 Ig fusion protein (Hoek, et al., supra), or a control Ig fusion protein (0.002 mg/ml).

In assays where FcεR (or the FcεR/IgE complex) was co-ligated with CD200Ra, DSP-1, LAIR-1, a goat anti-mouse F(ab')2 that binds to both mouse and rat antibodies (cat no. 115-006-062, Jackson Immuno Research, West Grove, Pa.) was added at 0.020 mg/ml. Further incubation at 37° C. was permitted to allow degranulation or cytokine secretion and the incubation was continued. Supernatant (0.02 ml) was removed and added to substrate to assess degranulation or secretion.

Degranulation and secretion were measured by separate methods. Degranulation was measured as follows. Supernatant (0.02 ml) was removed, e.g., at one hour after adding control or experimental antibodies, and transferred to 0.06 ml of 1.3 mg/ml p-nitrophenol-N-acetyl-B-D-glucosamide (Sigma, St. Louis, Mo.) in 0.1 M citric acid, pH 4.5. After 3-4 hours at 37° C., 0.1 ml of stop solution was added (0.2 M glycine, 0.2 M NaCl, pH 10.7) and $Abs_{405-650}$ was measured with a microplate reader (Molecular Devices, Sunnyvale Calif.). Cells were washed two times after removal of the supernatant. Cytokine secretion was measured as follows. Tumor necrosis factor-α (TNF-α) and interleukin-13 (IL-13) present in supernatants of mast cells were measured using cytokine specific ELISA kits (R & D Systems, Minneapolis, Minn.). Supernatants were collected after 18-30 hours of stimulation.

XIII. Cross-Linking OX2Ra (Inhibiting) and FcεRI (Activating) and Inhibition of Mast Cells.

Mouse CD200Ra is an inhibiting receptor, having a long cytoplasmic tail, though it lacks a classical ITIM motif. Mouse CD200Rb, c, and d are activating, and have short cytoplasmic tails and charged amino acids in their transmembrane regions, which may pair with DAP-12. Triggering these receptors results in secretion of a variety of cytokines. Human CD200Rb pairs with DAP-12, as does mouse CD200Rb.

Providing murine mast cells with IgE alone stimulates degranulation, while providing cells with IgE and anti-CD200Ra and cross-linking these two antibodies inhibits the degranulation. Human CD200Ra is homologous to mouse CD200Ra.

Murine mast cells were exposed to the following conditions, followed by assessment of degranulation (short term incubation) or of secretion of tumor necrosis factor-α (TNF-α) (long term incubation), as indicated. Media only (0% degran.; 0 ng/ml TNF-α); IgE only (100% degran.; 7.3 ng/ml TNF-α); anti-CD200Ra antibody only (0% degran.; 0 ng/ml TNF-α); IgE plus anti-CD200Ra antibody (100% degran.; 7.2 ng/m) TNF-α), and IgE plus anti-CD200Ra antibody plus the cross-linking agent goat anti-mouse Ig (17% degran.; 0.18 ng/ml TNF-α). Degranulation and TNF-α production were measured after incubating cells for 1 h and 6 h, respectively. "Zero" means below the level of reproducible detection.

XIV. Cross-Linking CD200Ra (Inhibiting) and FcεRI (Activating) and Inhibition of Human Mast Cells.

Degranulation and secretion by human mast cells was measured by a protocol involving addition of anti-IgE receptor antibody, which binds to IgE receptor, addition of anti-CD200R antibody, which binds to CD200R, and addition of goat anti-mouse F(ab')2, which binds to the anti-IgE antibody (adhering to IgE receptor) and to anti-CD200R antibody (adhering to CD200R). Control experiments involved variations of this protocol.

Whole cord blood cells were cultured in Yssels medium supplemented with stem cell factor (SCF) and IL-6 for 4-6 weeks. IL-4 and IgE were added to the culture for an additional 2 weeks. Cells were then plated at $10^6$ cells/well in 96 well flat bottom plates. An inhibitory antibody (anti-CD200Ra antibody) or control antibody (mouse Ig) was then added. After 20 min incubation, anti-IgE receptor antibody was added to give a concentration of 20 ng/ml. After 20 min of further incubation, the wells were washed and the crosslinker (goat anti-mouse antibody) was added. The mixture was incubated for 1 h, and the supernatant withdrawn and used for degranulation assays, as assessed by tryptase release. Tryptase assays were performed with the substrate N-alpha-benzyl-DL-arginine p-nitroanilide hydrochloride (BAPNA) with color measurement at 405-570 nm.

Degranulation (tryptase release) was maximal with addition of anti-IgE receptor antibody and control antibody (mouse Ig). Maximal tryptase release, under these conditions, resulted in $Abs._{405-570}$=0.44-0.51. In incubations with anti-CD200Ra, rather than control antibody, titrating levels of anti-CD200Ra antibody were used (0-1000 ng/ml anti-CD2000Ra antibody). Different levels of antibody were used in separate incubation mixtures. Use of increasing anti-CD200Ra antibody levels resulted in the progressive inhibition of tryptase release, where maximal inhibition ($Abs._{405-570}$=0.05) occurred with about 1000 ng/ml anti-CD200Ra antibody. Inhibition resulting in 25% maximal tryptase release occurred at about 200 ng/ml anti-CD200Ra antibody. The results demonstrate that cross-linking CD200Ra with IgE receptor prevents IgE receptor-dependent degranulation.

XV. Cross-Linking DSP-1 (Inhibiting) and FcεRI (Activating) and Inhibition of Human Mast Cells.

Cells were prepared and assays were conducted as described above (Example V), except that the added inhibitory antibody was anti-DSP-1 antibody, rather than anti-CD200R antibody. Degranulation (tryptase release) was maximal with addition of anti-IgE receptor antibody plus control antibody (mouse Ig). Maximal tryptase release, under these conditions, resulted in $Abs._{405-570}$=0.44-0.51. Titrating levels of anti-DSP-1 antibody were used (0-1000 ng/ml anti-DSP-1 antibody). Different levels of anti-DSP-1 antibody occurring in separate incubation mixtures. Use of increasing anti-DSP-1 levels resulted in the progressive inhibition of tryptase release, where maximal inhibition ($Abs_{405-570}$=0.08) occurred at about 40 ng/ml anti-DSP-1 antibody, as well as at higher concentrations of anti-DSP-1 antibody. Inhibition resulting in 25% maximal tryptase release occurred at about 8 ng/ml anti-DSP-1 antibody. The results demonstrate that cross-linking DSP-1 with IgE receptor prevents IgE receptor-dependent degranulation.

XVI. Cross-Linking LAIR-1 (Inhibiting) and FcεRI (Activating) and Inhibition of Human Mast Cells.

Cells were prepared and assays were conducted as described above (Examples V and VI), except that anti-LAIR-1 antibody was used. Anti-LAIR-1 antibody was used at only two concentration (0 and 50 ng/ml). Where incubations contained only added activating antibody (anti-IgE receptor antibody), tryptase release was about $Abs_{405-570}$=0.69 (defined as maximal). Where incubations contained activating antibody (anti-IgE receptor) plus anti-LAIR-1 antibody (50 ng/ml), tryptase release was inhibited, and was about 10% maximal ($Abs_{405-570}$=0.07). Control incubations containing no activating antibody, with or without anti-DSP-1, all resulted in very little tryptase release ($Abs_{405-570}$=0.06). The results demonstrate that cross-linking LAIR-1 with IgE receptor prevents IgE receptor-dependent degranulation.

Many modifications and variations of this invention, as will be apparent to one of ordinary skill in the art can be made to adapt to a particular situation, material, composition of matter, process, process step or steps, to preserve the objective, spirit and scope of the invention. Many of the inhibiting receptors and activating receptors are promiscuous, meaning that any given inhibiting receptor may inhibit the activity of any one of a variety of different activating receptors, and that any given activating receptor may be inhibited by any one of a number of different inhibiting receptors. All such modifications are intended to be within the scope of the claims appended hereto without departing from the spirit and scope of the invention. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

What is claimed is:

1. A method for inhibiting the activation of a cell, said method comprising administering a bispecific antibody which binds to:
   (a) an inhibitory receptor expressed on the cell and
   (b) an activating receptor,
wherein the inhibitory receptor is OX2Ra and the activating receptor is FcεRI.

2. The method of claim 1, wherein the bispecific antibody comprises a chemical linking agent that is covalently incorporated into the bispecific antibody.

3. The method of claim 1, wherein said bispecific antibody is a single polypeptide chain antibody.

4. The method of claim 1, wherein the bispecific antibody is humanized.

5. The method of claim 1, wherein the bispecific antibody is administered in conjunction with an agent that stimulates expression of an inhibiting receptor or an activating receptor, wherein said agent is selected from the group consisting of granulocyte colony stimulating factor and interferon-γ.

6. The method of claim 1, wherein the bispecific antibody is administered in conjunction with a therapeutic selected from the group consisting of an anti-inflammatory agent, a chemotherapeutic agent, an immunosuppressive agent, and an anti-malarial agent.

7. The method of claim 6, wherein the anti-inflammatory agent is selected from the group consisting of corticosteroids, glucocorticoids, soluble tumor necrosis factor receptor, and antibodies against tumor necrosis factor.

8. The method of claim 6, wherein the chemotherapeutic agent is selected from the group consisting of methotrexate, vincristine, and cyclophosphamide.

9. The method of claim 1, wherein said administration is in vivo or to cultured cells.

* * * * *